US012578350B2

(12) United States Patent
Kunkel et al.

(10) Patent No.: US 12,578,350 B2
(45) Date of Patent: Mar. 17, 2026

(54) SYSTEM AND METHOD FOR COAGULATION AND PLATELET FUNCTION RELATED DATA COLLECTION AND ANALYSIS

(71) Applicant: FloBio LLC, Philadelphia, PA (US)

(72) Inventors: Mark Allen Kunkel, Lawrenceville, NJ (US); Jason Matthew Rossi, Philadelphia, PA (US); Gary Lee Feiss, Telford, PA (US)

(73) Assignee: FloBio, LLC, Philadelphia, PA (US)

( * ) Notice: Subject to any disclaimer, the term of this patent is extended or adjusted under 35 U.S.C. 154(b) by 0 days.

(21) Appl. No.: 19/240,279

(22) Filed: Jun. 17, 2025

(65) Prior Publication Data

US 2025/0389738 A1      Dec. 25, 2025

Related U.S. Application Data

(60) Provisional application No. 63/661,960, filed on Jun. 20, 2024.

(51) Int. Cl.
 *G01N 33/86* (2006.01)
 *B01L 3/00* (2006.01)
(52) U.S. Cl.
 CPC ........ *G01N 33/86* (2013.01); *B01L 3/502715* (2013.01); *B01L 2200/16* (2013.01);
 (Continued)
(58) Field of Classification Search
 CPC ............... G01N 33/86; B01L 3/502715; B01L 2200/16; B01L 2300/0636;
 (Continued)

(56) References Cited

U.S. PATENT DOCUMENTS 8,404,724 B2 *   3/2013   Sinha ..................... A61K 31/40
                                                      514/822
2022/0283190 A1 *   9/2022   Frydman ........... B01L 3/502715

FOREIGN PATENT DOCUMENTS

WO     WO 2022/094608      *   5/2022   ................ B01L 3/00
WO     WO 2024/163843 A1 *   8/2024   ............. G01N 33/86

OTHER PUBLICATIONS

Brinkman, H. et al., Reversing direct factor Xa or thrombin inhibitors: Factor V addition to prothrombin complex concentrate is beneficial in vitro, Res Pract Thromb Haemost. 2022:6:e12699. doi: 10.1002/rth2.2699.

(Continued)

*Primary Examiner* — Christine T Mui
(74) *Attorney, Agent, or Firm* — McCarter & English, LLP

(57) ABSTRACT

A system for detecting and quantifying platelet function and coagulation function within a biological sample is provided. The system includes a detection instrument with computing capability. The system includes an assay device capable of receiving a biological sample. Introduction of the biological sample into the assay device results in a biological process by which fibrin and platelets may accumulate at a reaction zone of the assay device. The assay device is capable of receiving one or more chemical reagents compatible with the biological sample and usable for detecting the accumulation of the fibrin and platelets within the reaction zone. The fibrin and platelets, and their associated signals, accumulated at the reaction zone of the assay device are usable to determine at least one of a platelet function, a coagulation function, platelet normalcy, fibrin normalcy, platelet response to a drug, and coagulation response to a drug, within the biological sample.

16 Claims, 30 Drawing Sheets

(52) U.S. Cl.
CPC .................. *B01L 2300/0636* (2013.01); *B01L 2300/0819* (2013.01); *B01L 2300/0864* (2013.01); *B01L 2300/0883* (2013.01)

(58) Field of Classification Search
CPC ..... B01L 2300/0819; B01L 2300/0864; B01L 2300/0883
USPC .......................................................... 436/69
See application file for complete search history.

(56) References Cited

OTHER PUBLICATIONS

Cawthern, KM. et al., Blood coagulation in hemophilia A and hemophilia C, Blood, vol. 91 (12), p. 4581-4592 (1998).

Dargaud, Y. et al., Platelet-dependent thrombography: a method for diagnostic laboratories, British Journal of Hematology, vol. 134 (3), p. 323-325 (2006).

International Search Report and Written Opinion from related International Patent Application No. PCT/US2025/033796 issued Sep. 3, 2025.

Kitamura, Y. et al., Spectrophotometric determination of platelet counts in platelet-rich plasma, International Journal of Implant Dentistry, vol. 4 (29) (2018)).

Lipowsky, H. et al., Hematocrit determination in small bore tubes by differential spectrophotometry, Microvascular Research, vol. 24 (1), p. 42-55 (1982).

Liu, Y et al., Fluorescent peptide for detecting factor XIIIa activity and fibrin in whole blood clots forming under flow, Res. Pract. Thromb. Haemost., 7;8(1):102291 (Dec. 2023), doi: 10.1016/j.rpth. 2023.102291, PMID: 38222077, PMCID: PMC10787300).

Mann, K.G. et al., Citrate anticoagulation and the dynamics of thrombin generation, Journal of Thrombosis and Hemostasis, vol. 5 (10), p. 2055-2061 (2007).

Mattley, Y. et al., Light scattering and absorption model for the quantitative interpretation of human blood platelet spectral data, Photochem Photobiol., vol. 71 (5), p. 610-619 (2000).

Rand, M.D. et al., Blood clotting in minimally altered whole blood, Blood, vol. 88 (9), p. 3432-3445 (1996).

Rossi, A Scalable, Point-of-Care, Microfluidic Approach for Assessing Thrombosis and Hemostasis, A Dissertation in Chemical and Biomolecular Engineering Present to the Faculties of the University of Pennsylvania, 2021.

Tatsumi, K. et al., Thermal Characteristics Measurement of Fibrin Reaction and Clot Formation in Venous Thrombosis Using Microchannel Flow, 16th International Heat Transfer Conference, Aug. 10-15, 2018, Beijing China.

Sugihara-Seki, M. et al., Margination of Platelet-Sized Particles in the Red Blood Cell Suspension Flow through Square Microchannels, Micromachines, 12, 1175 (2021) (https://doi.org/10.3390/mi12101175).

* cited by examiner

Vasoconstriction

Red Blood Cell

Platelet Plug

Platelet Plug
Formation

Platelet

Fibrin

Clot Formation

Fibrin

Time Point

FI

Example Fibrin Function Classification

| FIBRINE50 | | | SD Ranges | | Percent Ranges |
|---|---|---|---|---|---|
| +1.0SD | 40.02 | AENORMAL | Range <40.02% | AENORMAL | Range >162% |
| +0.5SD | 32.36 | HIGH | Range 32.4 - 40.02 | HIGH | Range 132 - 162% |
| +0.25SD | 28.53 | HIGH NORMAL | Range 28.54 - 32.36 | HIGH NORMAL | Range 117 - 131% |
| Average | 24.70 | NORMAL | Range 20.87 - 28.53 | NORMAL | Range 84 - 116% |
| -0.25SD | 20.87 | LOW NORMAL | Range 17.04 - 20.86 | LOW NORMAL | Range 69 - 83% |
| -0.5SD | 17.04 | LOW | Range 9.38 - 17.03 | LOW | Range 38 - 68% |
| -1.0SD | 9.38 | AENORMAL | Range 0 - 9.37 | AENORMAL | Range 0 - 37% |

FIG. 5

BLOOD CELLS

| Variable (Common Abbreviations) | Units | Values |
|---|---|---|
| Hematocrit (HCT) or Packed cell volume (PCV) | Percent or mL red cells/dL blood, respectively | M = 42-51 F = 36-46 |
| Hemoglobin (Hb, Hgb) | g/dL blood | M = 14-18 F= 12-15 |
| Red cell count (RBC, RCC) | $10^6/\mu L$ or $10^{12}/L$ | M = 4.5-6.0 F = 4.1-5. 1 |
| Mean cell volume (MCV) | fL/cell | M = 80-96 F = 79-94 |
| Mean cell hemoglobin (MCH) | pg/cell | 27-33 |
| Mean cell hemoglobin concentration (MCHC) | g/dL red cells | 33-36 |
| Red cell distribution width (RDW) | Percent | < 15 |
| Reticulocyte count | Percent of red cells | 0.5-1.5 |
| Reticulocyte hemoglobin (CHr) | pg/cell | 27-33 |
| Total blood volume (TBV) | mL/kg | 65-85[+] ; 55-75[#] |
| Plasma volume (PV) | mL/kg | 39-44 |
| Red cell mass (RCM) | mL/kg | 25-35 |
| Platelet count | $10^3/\mu L$ or $10^9/L$ | 175-450 |
| White cell count (WBC, WCC) | $10^3/\mu L$ or $10^9/L$ | 4.8-10.8 |
| Absolute monocyte count | $10^3/\mu L$ or $10^9/L$ | 0.3-0.8 |
| Absolute neutrophil count | $10^3/\mu L$ or $10^9/L$ | 1.8-7.7 |
| Absolute lymphocyte count | $10^3/\mu L$ or $10^9/L$ | 1.0-4.8 |
| CD3-positive lymphocytes | $10^3/\mu L$ or $10^9/L$ | 700-1900 |
| CD4-positive lymphocytes | $10^3/\mu L$ or $10^9/L$ | 400-1400 |
| CD8-positive lymphocytes | $10^3/\mu L$ or $10^9/L$ | 200-700 |
| CD19-positive lymphocytes | $10^3/\mu L$ or $10^9/L$ | 50-375 |

FIG. 6A

| HEMOGLOBIN ELECTROPHORESIS' | | |
|---|---|---|
| Hemoglobin A1 | Percent of total hemoglobin | 96.1-99.0 |
| Hemoglobin A2 | Percent of total hemoglobin | 0.8-3.4 |
| Hemoglobin F | Percent of total hemoglobin | 0.0-1.2 |
| COAGULATION TESTS | | |
| Prothrombin time (PT) | Seconds to clot | 12-14 |
| International Normalized Ratio (INR) | None | 0.8-1.2 |
| Partial thromboplastin time (PTT) | Seconds to clot | 19-30 |
| Thrombin time | Seconds to clot | 10-15 |
| Closure time (PFA-100) Collagen/epinehrine (CEPI) | Seconds | <175 |
| Clot retraction | Percent in 1 hour | >40 |
| Fibrinogen | mg/dL plasma | 188-381 |
| D-Dimer | ng/mL | <400 |
| Factor II, V, and VII | Percent of normal mean | 50-150 |
| Factor VIII: c activity | Percent of normal mean | 50-200 |
| Willebrand factor activity | Percent of normal mean | 60-200[§] |
| Willebrand factor antigen | Percent of normal mean mg/L | 50-160[§] ~ 100 |
| Factor VIII-inhibitor | Bethesda units | 0-0.5 |
| Factor IX | Percent of normal mean Mg/L | 50-150 ~ 4.0 |
| Factor X | Percent of normal mean mg/L | 50-150 ~ 10 |
| Factor XI | Percent of normal mean mg/L | 50-150 ~ 7.0 |
| Factor XII | Percent of normal mean | 50-150 |
| Factor XIII | Percent of normal mean | 70-130 |
| $\alpha$2- antiplasmin | Percent of normal mean | 80-120 |

FIG. 6B

| Plasminogen | Percent of normal mean | 80-120 |
|---|---|---|
| Antithrombin:<br>    Functional assay<br>    Immunologic assay | <br>Percent of normal mean<br>mg/dL | <br>80-120<br>22-33 |
| Protein C | Percent of normal mean<br>µg/mL | 70-140<br>3.0-5.0 |
| Activated protein C resistance | APC ratio | >1.5 |
| Protein S<br>    Total<br>    Free<br>    Free/total ratio | Percent of normal mean<br>µg/mL<br>µg/mL<br>Unitless | 65-140<br>20-25<br>6-10<br>~ 0.4 |
| Fibrin degradation products (latex particles) | µg/mL | <20 |
| Platelet Aggregation (in platelet-rich plasma)<br>    With collagen (2 µg/mL)<br>    With arachidonic acid (0.5 mM)<br>    With ADP 5 µM<br>    With ADP 10 µM<br>    With epinephrine (5 ... | | |

FIG. 6C

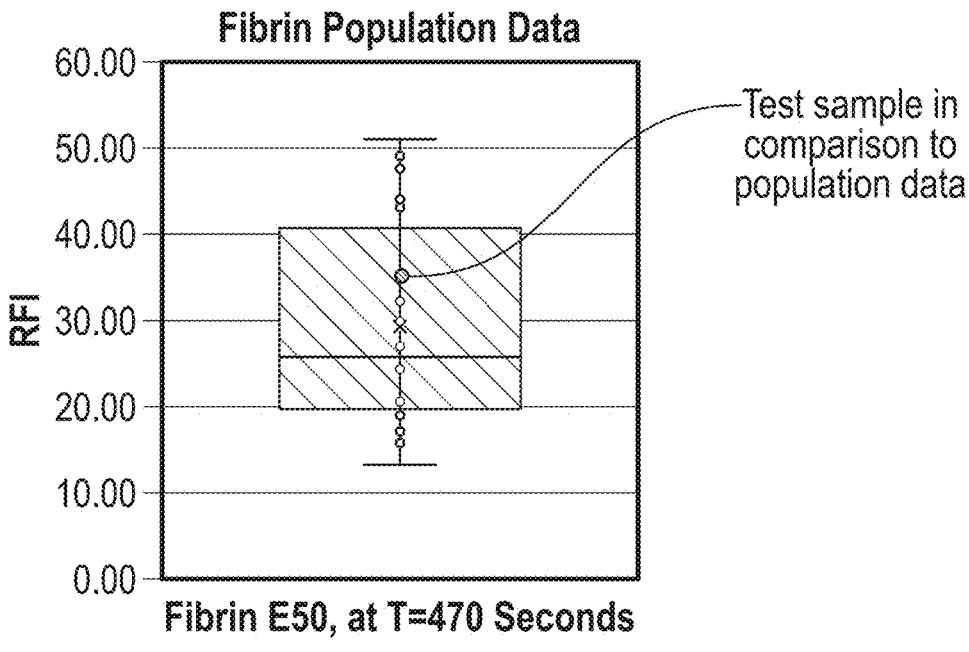

Test sample in comparison to population data

Maximum Value of the Data Set → x Outlier

Upper Fence = $Q_3$ + 1.5 x IQR

Maximum Value Before the Upper Fence

25% of Values

Whisker

Interquartile Range, IQR (The Box) IQR = $Q_3$-$Q_1$

25% of Values

25% of Values

75th Percentile, Third Quartile or $Q_3$

Median, 50th percentile, second quartile or $Q_2$

25th Percentile, First Quartile or $Q_1$

Whisker

25% of Values

Minimum Value Before the Lower Fence

Lower Fence = $Q_1$ - 1.5 x IQR x Outlier x Outlier ← Minimum Value of the Data Set

FIG. 7

Assay Fail Warning

Low Platelet Warning

Low Fibrin Warning

Low Overall Function Warning

100

102                         112

104

BLOOD FLOW 106  110    108                    116  114

100

104    102              112

25.5
mm 106                   110  108  116  114
Outlet                    Priming Inlet 75.5 mm Collagen/Tissue
Factor Scan or Manually Input the Capture ID Scan or Manually Input the Operator ID Scan or Manually Input the Patient ID Fibrin Function:          106.4%

Normal

Platelet Function:          97.1%

Normal

Scatterplot of Percent of Maximum vs Seconds

Statistics

| Variable | Etime | N | Mean | StDev | CoefVar | Minimum | Maximum |
|---|---|---|---|---|---|---|---|
| Fibrin_FI | E25 | 20 | 11.35 | 9.24 | 9.24 | 3.97 | 33.29 |
| | E50 | 20 | 21.76 | 14.14 | 14.14 | 7.82 | 50.92 |
| | E75 | 20 | 33.00 | 15.63 | 15.63 | 14.06 | 61.01 |

Fibrin FI

| Range | E50 | E75 |
|---|---|---|
| +2 SD | 50.04 | 64.26 |
| +1.5 SD | 42.97 | 56.445 |
| +1 SD | 35.9 | 48.63 |
| +0.5 SD | 28.83 | 40.815 |
| AVE | 21.76 | 33 |
| -0.5 SD | 14.69 | 25.185 |
| -1 SD | 7.62 | 17.37 |
| -1.5 SD | 0.55 | 9.555 |
| -2 SD | -6.52 | 1.74 |

| Statistics | | | | | | | |
| --- | --- | --- | --- | --- | --- | --- | --- |
| Variable | Etime | N | Mean | StDev | CoefVar | Minimum | Maximum |
| Paltelet_FI | E25 | 20 | 17.861 | 4.295 | 24.05 | 12.655 | 28.232 |
| | E50 | 20 | 38.49 | 8.49 | 22.06 | 27.38 | 56.67 |
| | E75 | 20 | 57.05 | 8.62 | 15.11 | 40.64 | 67.93 |

| | Fibrin FI | |
| --- | --- | --- |
| Range | E50 | E75 |
| +2 SD | 55.47 | 74.29 |
| +1.5 SD | 51.22 | 69.98 |
| +1 SD | 46.98 | 65.67 |
| +0.5 SD | 42.73 | 61.36 |
| AVE | 38.49 | 57.05 |
| -0.5 SD | 34.24 | 52.74 |
| -1 SD | 30.00 | 48.43 |
| -1.5 SD | 25.75 | 44.12 |
| -2 SD | 21.51 | 39.81 |

SYSTEM AND METHOD FOR COAGULATION AND PLATELET FUNCTION RELATED DATA COLLECTION AND ANALYSIS

CROSS-REFERENCE TO RELATED APPLICATION

The present application claims priority benefit to a US provisional application entitled "System and Method for Coagulation and Platelet Function Related Data Collection and Analysis," which was filed on Jun. 20, 2024 and assigned Ser. No. 63/661,960. The entire content of the foregoing US provisional patent application is incorporated herein by reference.

STATEMENT OF GOVERNMENT SUPPORT

This invention was made with government support under Award No. R44HL149480 awarded by the Department of Health and Human Services of the National Institutes of Health (NIH). The government has certain rights in the invention.

BACKGROUND

Assessment of bleeding and clotting risk in critical care environments may be difficult with traditional systems. Traditional systems are generally unable to create a testing environment that is analogous to the blood clotting physiology found in the human body, do not provide specific functional data on the key components of hemostasis (platelets and coagulation), and cannot provide results in a timeframe required for critical care decision making in emergent situations (e.g., emergency rooms, trauma bays, emergency surgery, or the like).

For example, FIGS. 1A-1C illustrate the physiology of hemostasis within the human body, with hemostasis involving a physiological response to vessel damage to arrest blood leakage involving both platelet aggregation and coagulation. FIG. 1A illustrates vessel injury with vasoconstriction, exposing collagen and tissue factor. FIG. 1B illustrates platelet plug formation through platelet aggregation. FIG. 1C illustrates clot formation and stabilization through the formation of a fibrin mesh. FIG. 2 illustrates the complex interconnection of intracellular and extracellular processes, and enzymatic reactions, that stimulate platelet deposition, thrombin generation, and coagulation.

SUMMARY

Definitions

Specific terminology is defined here to clarify specific elements of the disclosure.

The term "system" refers to the entirety of the technology in question, including the microfluidic device, reagents, imaging instrument, software, analytical methods, and reporting.

The term "device" refers to the microfluidic apparatus for producing fibrin and platelet signals.

The term "reagents" refers to the chemicals and drugs necessary to perform the assay.

The term "instrument" or "analyzer" refers to the imaging apparatus and associated computing hardware used to collect and process data from the device.

The term "analytics" refers to the methodology for converting the raw imaging data into clinical results.

The term "reporting" refers to the documentation of the analytical results.

As used herein, the term "fluidically" or "fluidic" refers to both static or active fluid communication between the ports and along the fluidic paths. Because the device is fluidically connected, flow within the device is possible at any time, in either direction (forward or reverse flow). As used herein, the term "active" flow or fluid communication refers to flow that is brought about by pressure or vacuum (i.e., a force) applied directly or indirectly to the fluidics of the device.

Unmodified Vs Modified Sample

A number of processes, effects, chemicals, and drugs are used in the exemplary system described herein. An important distinction is what is meant by a Modified or Unmodified Sample. A whole blood sample taken directly from a patient (whether containing drugs or not), and that same blood sample mixed with detection chemicals, is considered to be unmodified (as the term is used herein) because the behavior of the sample (the coagulation and platelet function) is not substantively changed from that of the in vivo behavior. For example, the addition of a platelet label, or the addition of a fibrinogen label does not intrinsically change the behavior of platelets nor of coagulation (e.g., fibrin accumulation).

A modified sample (as the term is used herein) is one in which the intrinsic behavior has been modified from the in vivo condition. For example, an anticoagulant or antiplatelet medication, and/or the reversal agent of those same drugs applied to the sample will assuredly change the behavior of the platelets and/or fibrin (i.e., coagulation). This is distinct from the fact that the sample may already contain some or all of these drugs inherently by way of the patient taking their prescribed medications, or other non-prescribed drugs or chemicals.

Drugs vs Chemicals

The utility of the system described herein is dependent upon the distinction of a drug vs a chemical. A drug (as used herein) is a specific compound formulated to derive a targeted biological effect. For example, the DOAC drug Dabigatran specifically targets (inhibits) thrombin. A chemical in this context (and as used herein) is a material that performs a specific targeted function within the assay, but is not designed or intended to direct or influence biological pathways or function. For example, a platelet labeling chemical is used to fluorescently tag platelets. But, this chemical does not affect the way in which platelets interact biologically in the formation of a clot.

Fluorescent Intensity Vs Relative Fluorescent Intensity

Fluorescent intensity (FI) (as used herein) generally refers to the raw, measured photon output of the biological signal being measured, without modification. Relative fluorescent intensity (RFI) (as used herein) generally refers to a modified fluorescent intensity that provides utility for analysis, such as improving signal to noise, or in its ability to be compared across or within data sets. For example, subtraction of background signal from the FI creates a relative intensity value based upon the removal of the background data. Data collected from different bit depth cameras could be made relative to one another by dividing all average intensity values by the maximum bit depth of the camera being used. A multitude of possible useful relationships could be used to relate raw pixel intensity to a common factor. This process is well known to those in the art of fluorescent microscopy. For the sake of expediency, the terms FI and RFI are considered interchangeable herein unless specifically noted otherwise.

Embodiments of the present disclosure provide for general and specific systems wherein the state of a patient's hemostatic function can be determined by measuring platelet and fibrin accumulation simultaneously, with accumulation of platelets, and fibrin as the reporting signals. Because hemostasis involves both platelet function and coagulation, the system evaluates both together to have a clear and accurate sense of a person's state of hemostatic function. While platelets (a subcellular component of hemostasis) are distinct from coagulation (an enzymatic reaction cascade), the two are intimately related to one another. Platelet binding to collagen and subsequent activation is a preemptive step in initiating a stabilized coagulation cascade, with degranulating platelets releasing a number of compounds that facilitate and stimulate coagulation as well as additional platelet accumulation. This process is affected by many co-factors (including exposed membrane phospholipids) that support the assembly of tenase and prothrombinase complexes. The terminal coagulation protease, thrombin, cleaves fibrinogen to form fibrin monomers that allows for the formation of a fibrin polymer. Fibrin polymer then creates a mesh around aggregating platelets to form a stabilized clot. In addition to catalyzing fibrin, thrombin is also a potent activator of platelets. Therefore, modulators of platelet function specifically (such as platelet targeting drugs) can also have differential levels of impact on fibrin formation, and vice versa. Thus, the two are intimately intertwined.

In general, blood products given to patients can have an immediate effect on platelet and/or fibrin function. Packed red blood cells affect hematocrit, which directly affects platelet margination and therefore also affects concentration in the cell free layer. Direct purified platelet addition immediately increases platelet function. Fresh frozen plasma contains all of the cofactors for coagulation and four-factor prothrombin concentrate (4-FPCC) contains key co-factors for coagulation that can be used both for bleeding events, and to reverse the effects of anti-coagulants like warfarin. (See, e.g., Horstman, E. E. et al., Plasma Products for Transfusion: An Overview, Department of Laboratory Medicine, Yale University School of Medicine, New Haven, CT, USA, Vol. 7 (March 2022)). Therefore, blood product use and stewardship directly requires the need to monitor both platelet and coagulation function.

Hemostatic equilibrium is a key aspect of normal hemostatic function where the body regulates both platelet function and coagulation so as not to create a physiologic response that is either too weak, nor too great, to injury or disease state. While in general there are "normal" measurable amounts of platelets, fibrinogen and other coagulation factors circulating in the blood, there are a multitude of additional factors that can influence any one individual's hemostatic response to injury or disease, thereby creating a potentially wide range of "normal" function. This represents a major hurdle for diagnostic evaluation of hemostatic function where only one aspect of the hemostatic cascade (either fibrin or platelets) is evaluated. The system described herein avoids this complication by evaluating the functional state of both platelets and overall coagulation, not just quantity of those factors.

Many factors can disturb the normal functioning of platelets and the coagulation cascade. These include, e.g., drugs, illness, disease, genetics, certain foods, physical injuries, combinations thereof, or the like. Published research shows that, for example, physical trauma to the body can lead to a dysfunction of platelet activity. COVID-19 infection has been shown to lead to hyper coagulation, that can lead to inappropriate clot formation and death. Suppression or enhancement of platelet function and/or coagulation can lead to either severe bleeding events or hyper-clotting events, respectively, that can complicate medical care, and even lead to death. Certain medical conditions that require medication or procedures that modify platelet function and/or coagulation (such as anti-coagulant or anti-platelet drugs, pro-coagulant drugs, blood transfusions, packed red blood cells, platelet therapy, or the like) can also lead to abnormal clotting and/or bleeding events that can cause iatrogenic injury or even death, with rapid onset.

From a medical perspective, general clotting function (hemostasis) is distinct from the medical process of preventing abnormal clotting (thrombosis) that is not related to an injury. For example, direct-acting oral anticoagulants (DOACs) that directly suppress coagulation function are taken by patients to prevent venous thromboembolism (VTEs), exacerbated by long term medical conditions, such as cardiac abnormalities and arrhythmias like atrial fibrillation (aFib). In some instances, prevention of a clot can be of paramount importance, to avoid a stroke or heart attack, for example. This is distinct from preventing a clot formed by a direct physical injury (a short-term process), because many patients are placed on DOAC therapy long term (months or years), and therefore have disturbed clotting behavior over long periods of time. In emergency critical care environments then, the detailed and accurate determination of whether a patient's hemostatic function is normal or not (whether affected by anti-coagulants, or anti-platelet medications or not) would be essential to properly managing the patient's increased bleeding risk. In conventional emergency critical care environments, the only available information may be if the patient is prescribed one of these drugs, and possibly when their last dose was taken (if this information is available at all). And even when this information is known, in such circumstances, the actual state of hemostasis within the patient can be difficult, if not impossible, to a certain a priori. The exemplary systems discussed herein provide an accurate and detailed determination of a patient's platelet function and their coagulation function. In some embodiments, the systems discussed herein can be also be used to detect aberrations in hemostatic function caused by novel oral anticoagulants (NOACs), direct-acting oral anticoagulants (DOACs), target-specific oral anticoagulants (TSOACs), and/or novel platelet targeting drugs, and/or drugs targeting other upstream or downstream aspects of the hemostatic cascade.

In the simplest case, a patient's blood is passed over a reaction zone where platelet and coagulation activators have been placed. For example, common activators include collagen and lipidated tissue factor (LTF), but others could be used that activate either or both the intrinsic or extrinsic coagulation pathways, as well as platelet binding and degranulation. As whole blood flows over the reaction zone, platelets can become bound to the collagen by way of their collagen receptors, which activate the platelets. LTF in combination with factor VIIa and other co-factors activates the coagulation cascade. This activation then recruits more platelets to the clotting zone, and activated thrombin catalyzes the formation of fibrin from soluble fibrinogen. This reaction is self-sustaining and additional platelet and fibrin accumulation increase over time, to the point where the flow of blood may be occluded. The reaction zone can include only one reactant (collagen), or more than collagen and LTF (e.g., von Willebrand Factor, (vWF)).

Blood from a healthy, uninjured person would produce a specific profile of platelet and fibrin accumulation over time, all other conditions being equal. Individual variances between healthy, uninjured persons would produce a distribution of normal hemostatic function around an overall average population function. This would provide for a boundary of conditions where signals outside of this normal range would constitute a distribution of "abnormal" platelet or coagulation function. In some embodiments, the assay could distinguish normal from abnormal platelet and coagulation function by a percentage or percentiles (for example) from the normal average (however this would not identify where the abnormal behavior was coming from (e.g., drugs, injury, disease, or the like).

Method for Determining Fibrin Function

Fibrin accumulation is a direct functional measure of thrombin activity, as thrombin is the activated serine protease that cleaves fibrinogen (a precursor) into fibrin. By examining the fibrin accumulation within the device from multiple healthy donors, an average time-based curve of fibrin accumulation over time, at the device's reaction zone, can be developed. Fibrin function for a test sample can then be defined by the accumulation of fibrin at the reaction zone of the device, in comparison to an average fibrin accumulation as found in a healthy normal population. Fibrin activity data is first collected from a population of healthy normal donors (typically adult), where the donor is not under the influence of a coagulation inhibiting drug, nor has a known coagulation, bleeding, or platelet disorder, is not pregnant, is generally in good health, and has no other conditions that would create a coagulopathy. Typically at least 10 donors and as many as 100 donors could be analyzed for this purpose, although more or less could be utilized. Each donor's blood is drawn and analyzed on the fluidic device, and fluorescent intensity relating to fibrin accumulation is recorded over time (over the course of the assay, which is generally 15 minutes). The coagulation activity of the device's reaction zone is a critical aspect that can modulate the level of fibrin accumulation. Therefore, the level of collagen and LTF in the reaction zone, for example, should be the same when testing the healthy donor population, as when testing the biological test sample.

The accumulated healthy donor data is then averaged at each data capture point, over the course of the assay, to create a single average fibrin function curve based upon the average relative fluorescent intensity. (FIGS. 3A and 3B). Standard statistical analysis can also be performed on this data to calculate the median, standard deviations, maximum rate of accumulation, and the like. At any selected time point within the average fibrin function curve, a comparison can be made to the relative fibrin fluorescence of a test sample. For example, a test sample with a coagulation defect could be run on the assay device, and fibrin signal accumulated over time. At a specific time point where fibrin function is measurable, the fibrin Fluorescent Intensity (FI) of the test sample can be compared to the fibrin FI of the average population data. Common points in time when this would be most useful include T50 (or half max of the Fibrin RFI), point of highest rate of RFI increase, or the like, although other points in time may be equally useful. Importantly, the point in time being evaluated is determined by the population data, and not the test sample data, as the test sample is being compared to the population data. Dividing the test sample fibrin RFI by the population fibrin RFI (×100) gives a percentage of function of the test sample fibrin signal in relation to the average population data. For example, if the test sample fibrin RFI was 55, and the population average fibrin signal at the same time point in the assay was 75, then the percent fibrin function of the test sample would be (55/75)*100 or 73.33% fibrin function (approximately, due to rounding error).

Since the test sample result is compared to a population of data, inaccuracy relating to determining individual test sample condition is, in part, directly proportional to the healthy population size, and its distribution of data. The larger the healthy population, the more representative the population data is to the general expected value for any test sample. It is envisioned that specific populations could be developed that present unique challenges to understanding coagulation function. For example, a healthy population of children could be developed; or a population of healthy neonates could be developed; or a population that is sex based (all female, for example); or an aged healthy population (over age 65) could be developed. Whatever the population basis for the comparison, the fibrin signal of any test sample, matched to its reference population, can be compared functionally, provided the comparison is made at the same point in time within the assay (e.g. if the population data is evaluated at T50, then also, the test sample should be evaluated at the same point in time as the T50 of the population data). To restate, the selection of the time by which the fibrin signal in the test sample is evaluated is not determined by a characteristic of the test sample; rather, it is determined by the characteristic of the population. For example, if the half-max of the population fibrin data is at 560 seconds, then the fibrin signal at 560 seconds within the test sample data (regardless of whether this point is half max for the test sample) is the fibrin value (RFI) used for comparison to the population fibrin value, at that point in time.

Method for Determining Platelet Function

Platelet accumulation at a clot site is a direct functional measure of platelet activity, as platelet's are activated by collagen within the active zone of the assay device. By examining the platelet accumulation within the device for multiple healthy donors, an average time-based curve of platelet accumulation over time, at the devices reaction zone, can be developed. Platelet function for a test sample can then be defined by the accumulation of platelets at the reaction zone of the device, in comparison to an average platelet accumulation as found in a healthy normal population. Platelet activity data is first collected from a population of healthy normal donors (typically adult), where the donor is not under the influence of a platelet inhibiting drug, nor has a known platelet, bleeding or coagulation disorder, is not pregnant, is generally in good health, and has no other conditions that would create platelet dysfunction. Typically at least 10 donors and as many as 100 donors could be analyzed for this purpose, although more or less could be utilized. Each donor's blood is drawn and analyzed on the fluidic device, and fluorescent intensity relating to platelet accumulation is recorded over time (over the course of the assay, which is generally 15 minutes). The platelet activity of the device's reaction zone is a critical aspect that can modulate the level of platelet accumulation. Therefore, the level of collagen and LTF in the reaction zone, for example, should be the same when testing the healthy donor population, as when testing the biological test sample.

The accumulated healthy donor data is then averaged across time to create a single average platelet function curve based upon the average relative fluorescent intensity. (FIGS. 4A and 4B). Standard statistical analysis can also be performed on this data to calculate the median, standard deviations, maximum rate of accumulation, and the like. At any selected time point within the average platelet function curve, a comparison can be made to the relative platelet fluorescence of a test sample. For example, a test sample with a platelet defect could be run on the assay device, and platelet signal accumulated over time. At a specific time point where platelet function is measurable, the platelet Fluorescent Intensity (FI) of the test sample can be compared to the platelet FI of the average population data. Common points in time when this would be most useful include T50 (or half max of the platelet RFI), point of highest rate of RFI increase, or the like, although other points in time may be equally useful. Importantly, the point in time being evaluated is determined by the population data, and not the test sample data, as the test sample is being compared to the population data. Dividing the test sample platelet RFI by the population platelet RFI (×100) gives a percentage of function of the test sample platelet signal in relation to the average population data. For example, if the test sample platelet RFI was 32, and the population average platelet signal at the same time point in the assay was 60, then the percent platelet function of the test sample would be (32/60)*100 or 53.33% platelet function (approximately, due to rounding error).

Since the test sample result is compared to a population of data, relating to determining individual test sample condition is, in part, directly proportional to the healthy population size, and its distribution of data. The larger the healthy population, the more representative the population data is to the general expected value for any test sample. It is envisioned that specific populations could be developed that present unique challenges to understanding coagulation function. For example, a healthy population of children could be developed; or a population of healthy neonates could be developed; or a population that is sex based (all female for example); or an aged healthy population (over age 65) could be developed. Whatever the population basis for the comparison, the platelet signal of any test sample, matched to its reference population, can be compared functionally, provided the comparison is made at the same point in time within the assay (e.g., if the population data is evaluated at T50, then also, the test sample needs to be evaluated at the same point in time as the T50 of the population data). To restate, the selection of the time by which the platelet signal in the test sample is evaluated is not determined by a characteristic of the test sample, rather, it is determined by the characteristic of the population. For example, if the half-max of the population platelet data is at 520 seconds, then the platelet signal at 520 seconds within the test sample data (regardless of whether this point is half max for the test sample) is the platelet value (RFI) used for comparison to the population platelet value, at that point in time.

It will be apparent to anyone in the medical field that the measurement of "normalcy" would not be expected to be a distinct value for fibrin and platelets, but rather a range of values that represent the "normal" range of expected function. Therefore, within any given population, there is likely no one specific fibrin or platelet value that represents normal. All human beings (even healthy ones) are different in their blood makeup, and hence their platelet and fibrin function can be different in comparison to any other person, driven by genetics, over-all health, age, diet, prescription drugs, nutraceutical use, and multiple other factors. It can be concluded then that the population average for fibrin and platelet function is a generalized indicator of normal, where values above and below the average can be considered at differing levels of normalcy. Therefore, percentages of the population average can be used as a metric for determining "normal", "low normal" and "abnormal" platelet and fibrin values detected from a sample by the device. For example, a sample that has a fibrin signal that is only 10% below the population average might well be considered functionally normal from a hemostatic sense. In some embodiments, a normal fibrin signal can be, e.g., 0-10% inclusive, 1-10% inclusive, 2-10% inclusive, 4-10% inclusive, 5-10% inclusive, 6-10% inclusive, 7-10% inclusive, 8-10% inclusive, 9-10% inclusive, or the like, below the population average. As a further example, a fibrin signal that is 25% below the population average may well be considered "low normal". In some embodiments, a "low normal" fibrin signal can be, e.g., 20-25% inclusive, 21-25% inclusive, 22-25% inclusive, 23-25% inclusive, 24-25% inclusive, 19-26% inclusive, 18-27% inclusive, 20-28% inclusive, 20-30% inclusive, 25-50% inclusive, 26-50% inclusive, 30-50% inclusive, 35-50% inclusive, 40-50% inclusive, 45-50% inclusive, or the like, below the population average. As a further example, a fibrin signal that is 50% or more below the population average might well be considered "abnormal". In some embodiments, an "abnormal" fibrin signal can be, e.g., 50% or more, or the like, below the population average. The thresholds for "normalcy" can be preset or input into the system such that the device and/or system can determine the "normalcy" of the fibrin (and platelet) signals detected by the device. In some embodiments, similar thresholds can be used for the platelet signal determination. In some embodiments, a "normal" signal can be in the 0-25% inclusive range, a "low normal" signal can be in the 26-50% inclusive range, and an "abnormal" signal can be in the 50% or more range. In some embodiments, the bounds of risk can be clarified by collecting clinical data, and following up on outcomes for patients that test in different ranges.

By creating thresholds then, one can categorize the continuous variable output of fibrin or platelet RFI into a binned clinical evaluation of hemostatic normalcy. This binning process for example could be based upon simple percentages above and below the average or could be based upon standard deviations around the population average. From a practical perspective, these ranges can be set based upon actual clinical outcomes for patients within any given range of function. As an example FIG. 5 shows a table in which the fibrin RFI is binned using standard deviation (STD) around the population average. A similar table could be used for platelet RFI. Alternative binning indices could be used to delineate normalcy from deviations in normalcy (e.g. percentages, or basic thresholds). The process of binning ranges of values is not unique to this technology and is common practice in the medical field. For example, blood chemistry values and hematology values (cell counts) are entirely based upon "normal ranges", with "abnormalcy" being determined by the test samples deviation from this normal range. (See FIGS. 6A-6C; see also, e.g., Lichtman, Marchall A. et al., Table of Normal Values, Williams Manual of Hematology, (e Eds., McGraw-Hill Education (2017).)

Apart from a categorical method for evaluating normalcy, normalcy can also be evaluated and presented to the user by mathematical or statistical means. For example, the population data (both fibrin and platelet) that is used as the reference for normal can be shown as separate box-plots (fibrin and platelet), wherein the average, overall distribution, quartiles, and the extremes can all be shown in one graph. A test sample's fibrin and platelet signal can then be displayed overlaid on the population fibrin and platelet box plot to represent where this sample falls in relation to the population data. (See, e.g., FIG. 7) In this way, a clinician, for example could quickly compare and assess the test sample's numerical relationship to the population data to determine how "abnormal" or "normal" a test sample was, through a simple pictograph.

FI Corrections, Relative Fluorescent Intensity, and Normalization

For those skilled in the art of fluorescent imaging, there are well known, basic methods by which fluorescent imaging data can be improved. One of these methods is background correction, where signals from the biological assay are corrected to account for non-assay and assay-based "noise" that are not of biological value to the resulting output. Non-assay signals can come from the system itself (autofluorescence), extraneous light sources (e.g., device or room lighting), and/or from the assay device materials (fluorescence or autofluorescence). In addition, assay-based background can come from the reagents or chemicals used to fluorescently tag the resulting reaction. In this case, fluorescent background signal can come from the Alexa Fluor 488 anti-CD61 platelet Antibody, and the Alexa Fluor 594 fluorescent human fibrinogen used in the assay to label platelets and fibrin. Regardless of its origin, background fluorescence can be subtracted from the primary assay signal by a number of means. For example, the first five images of the analysis can be used to average the background signal to arrive at a background image that can then be used to subtract (on average or pixel by pixel) the background from all other developing signals. Additional methods generally used in fluorescent microscopy can also be used in the system.

Relating a fluorescent signal to a reference value is another practice of fluorescent data analysis where the signals across the image set are adjusted against a relative value, leading to the creation of an alternate set of pixel outputs called Relative Fluorescent Intensity, or RFI. For example, subtracting the background from the raw pixel intensities creates a relative fluorescent signal related to the background corrected value. For instance, a pixel value of 100 FI, after subtraction of a background of 10 FI, would have an RFI of 90. Multiple other reference values can be used to create a valid RFI value.

Normalization of fluorescent data is another practice and is useful for comparing across data sets. For example, data collected from cameras of different bit depth (8 bit, 10 bit, 12 bit) can be normalized to their maximum pixel value (or maximum average value within a region of interest), and therefore allow for direct comparison across data sets as each normalized data set is a range of values from 0 to 1. In addition, the fibrin signal and the platelet signal can be compared on the same scale if normalized to their respective maximums. Again, multiple factors and methods can be used to normalize the raw data. Equations 1 and 2 below illustrate determination of the normalized data.

$$x \text{ normalized} = (x - x \text{ minimum})/\text{range of } x \qquad (1)$$

$$x \text{ normalized} = a + (((x - x \text{ minimum})*(b-a))/\text{range of } x) \qquad (2)$$

where a is the minimum value and b is the maximum value of the custom normalization range.

Thresholding as a Means to Qualify Assay Performance

The development of the fibrin and platelet signal occurs over time as platelets and fibrin accumulate at the clot site. During this process, typically over 15 minutes, multiple thresholds can be defined as meaningful to the function of the assay, or to provide clinical insight into the activity of the sample. FIGS. 8A-8D are charts showing the assay fail warning (FIG. 8A), the low platelet warning (FIG. 8B), the low fibrin warning (FIG. 8C), and the low overall function warning (FIG. 8D). For example, an RFI value between 0 and the E50 could be chosen to evaluate the "initiation" of platelet or fibrin growth beyond the background. An RFI of <10 can be used to designate that a sample has developed sufficient signal (in comparison to the population data) to make a determination of functional behavior. In other words, if the platelet and fibrin signal never achieves a threshold value, then the assay is deemed to be a "fail" and a warning could be displayed at a user interface. Alternatively, if either the platelet or fibrin signal never achieves a minimum value, this can indicate severe platelet or coagulation inhibition, and a "low signal warning" could be displayed at the user interface. This can indicate, for example, that a patient has severely suppressed platelet or fibrin function, caused by an excess of inhibitor drug or some other biological effector that suppresses function. Additional RFI values (e.g., T25 or quarter max) can be used to evaluate the early growth of platelet and fibrin signal to provide an early warning to the clinician that the patient's platelet function or coagulation function is depressed beyond normal expectations, while the assay is still running. This can provide critical clinical data prior to the 15 minute assay completing, allowing clinicians the opportunity to make critical life-saving decisions earlier. This is possible as the system is capable of extracting data from the active clot sites as soon as they develop. This permits the system to collect, analyze and display data in real time as the assay progresses, providing useful results to the clinician as they develop. Such a system could provide early feedback on hyper-reactivity within the first 3 minutes of the assay.

Additional Methods for Evaluating Fibrin and Platelet Signals

It is anticipated that beyond the comparison to the population average, there are individual differences in fibrin and platelet behavior that could be delineated by additional methods of analysis. For example, within the development of the time-based curve for fibrin accumulation or platelet accumulation, there are multiple characteristics and inflection points that may present unique clinical signatures for any given sample. For example, the rate of signal development (the slope) can be compared between the test sample and the population data to determine if the rate of platelet or fibrin accumulation was substantially greater or less than the population average. A steep slope (high rate) could indicate a hyper-coagulation or hyper-active platelet state, while a shallow slope could indicate a hypo-coagulation or hypo-active platelet state, respectively. In some embodiments, a "normal" range can be 35-55 degrees inclusive, a "high normal" range can be 55-65 degrees inclusive, a "low normal" range can be 25-35 degrees inclusive, an "abnormal high" range can be 65-90 degrees inclusive, and an "abnormal low" range can be 0-25 degrees inclusive. When compared in conjunction to standard blood tests like a CBC, this information can be critical to the clinician in understanding the patient's overall hemostatic state. For example, if the patient's blood sample shows a normal platelet count, but a dramatically lower platelet activity (shallow slope), this would indicate platelet dysfunction. However, if platelet count was normal, and yet platelet activity very high (steep slope), this could indicate hyper-active platelet function. The same evaluation could be performed with fibrin. The system can therefore use this type of data analysis for fibrin and platelet behavior.

The slope could be determined at any point during the development of the resulting signal. However specific time points may be more beneficial than others. For example, the E50 or half max RFI point of the assay would represent a point in time where signal growth rate is stable and at its maximum. The slope can then be determined by a number of mathematical means. One simple example for determining slope is shown in FIGS. 9A and 9B for fibrin intensity and platelet intensity, respectively. For example, points are selected on either side of the half max, e.g. 40% of max and 60% of max RFI. From the coordinates of these two points, a simple slope equation can be used (Equation 3):

$$y2-y1/x2-x1 \qquad (3)$$

FIGS. 9C and 9D shows two alternative methods for determining changes in slope in real-time, or nearly real-time. FIG. 9C is a simple plot of the change in RFI between specific, adjacent time points during the analysis of the sample. The inflection point where the RFI stops increasing and starts to decrease would be an indicator of the maximal rate of change. In FIG. 9D, basic calculus is used to derive the angle of a right triangle formed by the x axis (time between images), and the Y axis (change in RFI). A simple trigonometric function then allows for the calculation of the angle at each point in time, as data is collected in real time, as shown in Equation 4 below.

$$\text{Tan}^{-1}(Y/X)=\Phi \qquad (4)$$

The angle or rate of change at a specific point in time, e.g., T50, can be compared to a range of values, similar to the SD and percent function ranges as shown in FIG. 5, to derive a general measure of "normalcy" for signal rate. More sophisticated methods are well known to those in the art and multiple methods for estimating slope (rate of change) are anticipated, such as numerical differentiation. Therefore, the examples provided herein are merely some of the methods that could be used by the system and alternative methods known in the industry can similarly be used by the system.

The maximum change in rate of signal development (e.g., a second derivative analysis) during the early stages of the assay (minutes 0-3 for example) can indicate when clotting begins to increase at a maximal rate. This can be referred to as a "clotting initiation time" indicating how active the patient's blood is, and providing a rapid initial assessment of general hemostatic function within the first 3 minutes of the assay. A high measured rate of fibrin or platelet accumulation can indicate a hyper-coagulation or hyper-thrombotic state (respectively) that would need to be addressed immediately by the clinician, even before the assay finished running. The near instantaneous rate of change in the slope can be calculated, for example, as shown in FIG. 9D. The maximum calculated angle is representative of the rate or steepness of signal development. Multiple methods can be devised to find similar relationships between the FI and the rate of increase in the FI.

In addition to the slope of the RFI, the shape of the curve for the developing signal can also provide additional information. For example, an increasing signal (either platelet or fibrin), followed by a sudden shift downward (less) in signal accumulation, can be indicative of a clot occlusion where blood flow within the microfluidic path is occluded either partially or completely. (See, e.g., FIG. 10) The occlusion has the effect of slowing or stopping blood flow, thereby suddenly reducing the accumulation of platelets or fibrin. The point in time where there this shift in signal development is seen can be referred to as an "occlusion time" or more informally as a "clotting time".

With respect to FIG. 10, an example of clinical data from a patient sample showing extreme flow disturbance at about 500 seconds due to blockage of the flow path from rapid platelet activity and clot formation is shown. The blockage stops flow, therefore rapidly reducing the rate of signal development. This deflection in signal development rate (an approximately 70% decrease in slope) is indicative of a flow path blockage. Any rapid slope change between consecutive data points is likely caused by a flow path obstruction, and should be removed from consideration. The rate can also be calculated from the RFI change between any two adjacent values, and this can be calculated in real time without the need for angles, "fitting" or derivatives.

The point of calculating these and other values automatically within the system is to avoid the need for the clinician to interpret the raw plotted data, and to especially avoid interpreting the raw image data. These values provide a simple means by which any sample can be quickly compared to the population data, or compared to any other sample, or comparisons made within a sample (e.g. comparison of platelets to fibrin).

ROI Finding and Data Extraction

Images taken by the system's camera can be stored for analysis at any time. In some embodiments, the images can be processed and analyzed by the system in substantially real time to extract useful data, and in the case of using fiducials, can occur from the very first image. This can be accomplished by finding a region of interest (ROI) within each clot site to extract the fluorescent data. The ROI can be the same size as the clot site, or could be smaller or larger than the clot site. Preferably an ROI that is smaller than the clot size allows for the elimination of pixels along the edges of the fluidic channel that have different shear rates than the center of the channel, and eliminates the leading and trailing edge of the clot which also can display different biochemical/fluid dynamic behavior than the center of the clot. The position of the ROI's can be determined by software by evaluating mechanical, visible and/or fluorescent fiducial marks on the assay device, so that the software can selectively calculate the physical location of each ROI by a coordinate position system from these "known" fiducial marks, placed very accurately during the manufacture of the device, in relation to the reaction zone of the device. (See, e.g., FIG. 11) Using this type of fiducial, the ROI's can be calculated from the very first image of the device's reaction zone and fiducials. Alternatively, the ROI's can be determined by using the resultant output of the assay itself, such that the resulting platelet and/or fibrin signal can be used to discriminate the boundaries of the ROI's for each clot site. While the fiducials support a solution for finding both the x and y coordinate position of the ROI, the x coordinate can be also be found by utilizing the sides of the fluidic flowpath itself. Since each flowpath is accurately manufactured to a specific size with a specific gap between each flowpath, these dimensions can also be used to set the position of the ROIs. The detection of the flowpaths, and/or the fiducials, can be by using white light (non-fluorescence) or a specific wavelength of light in conjunction with fluorescent markers can be used to find the flowpaths (in the case of the present assay, the platelet and fibrin labels themselves). In addition, alternate fluorescent materials with alternate fluorescent wavelengths can be used to find the ROI's or channels. For example, microparticles with 405 nm fluorescence can be co-introduced with the sample, or run in a separate lane of the device. These particles can accumulate at the reaction zone being sensitive to the collagen or tissue factor, or some other factor bound at the reaction zone. The accumulation of these 405 nM signals could then be used to selectively identify the ROI's, and flowpaths, without interference with the signals from fibrin or platelets.

Measurement of Platelet and Coagulation Function from Specific Drug Effect

Due to the flexible nature of the system in determining both platelet and coagulation function simultaneously, the system can be used to determine the response of a patient's blood to drugs that affect platelets or coagulation. For example, patient drug dosing is typically derived through a body mass calculation, however, not all patients respond to a mass dosed drug equivalently. In fact, some patients have varied responses to a "correctly" dosed drug. The system could be used, for example, to measure a patient's reactivity in real time to a specific dose of drug. The drug in question can be mixed with a small bolus of patient blood outside the device (in vitro), and the drug spiked blood then analyzed on the system. (See, e.g., FIGS. 12A and 12B). In this way, a clinician could verify a dose specific reactivity for each given patient as every patient has a unique profile of absorption, distribution, metabolism and excretion of drugs. This is particularly relevant in the development of novel drugs where dose response behavior is being determined through clinical trial of ascending drug doses, both in healthy and diseased patients. After dosing the patient, the patient's hemostatic function could be tested periodically with the system, allowing for adjustments to drug dosing using in vivo results.

With reference to FIGS. 12A and 12B, device data showing how fibrin signal and platelet signal respond to spiked drugs is illustrated. In this example, dabigatran was spiked into a normal healthy blood sample (external to the device) to determine the samples response to drug level when analyzed on the device. Dabigitran was spiked from 0 nM (control) to 250 nM, demonstrating fibrin's clear dose response to dabigatran, a direct thrombin inhibitor. Platelet response from the same sample, collected at the same time, is muted to drug dosing as expected, as dabigatran does not directly act on platelet function.

In some embodiments, methods for performing the evaluation of platelet function and coagulation can be performed by the system in several ways, but should utilize blood that is under flow. Traditional systems often utilize constrained blood samples with minimal or controlled agitation (such as stirring) to measure clotting function. However, these methods are not able to distinguish the individual activity of coagulation from platelet function, may utilize fractionated blood products (such as plasma) that are only a proxy for a whole blood sample, and do not mimic the effective behavior of blood in vivo. The very act of fractionating blood into its constituent components also creates an artificial environment that is unlike that found in the body. Therefore, the activity of platelets and the coagulation pathway in this scenario is neither representative of in vivo blood behavior, nor of biochemical distribution of reactants found in the body. Other traditional systems that attempt to analyze blood under flow generally make no attempt to reproduce the actual blood flow characteristics of the body, resulting in an assay that does not represent the characteristics or activity of blood in the body. Traditional devices that attempt to recapitulate blood flow often do not attempt to assess both platelet function and coagulation concurrently, providing an incomplete answer to overall hemostasis function. The ability then to accurately determine platelet and coagulation function concurrently, under physiologic conditions, is absolutely critical to evaluating hemostatic function, in real-time. The systems discussed herein provide such determination.

Several in vivo key characteristics determine blood behavior as it relates to platelet function and coagulation: (i) shear rate at the surface of the reaction zone; (ii) flow rate/volume of blood; (iii) surface area of the injury site; (iv) temperature; (v) hematocrit; (vi) platelet count and function; (vii) fibrinogen levels; and/or (viii) coagulation co-factor levels. Platelets, for example, have over 10 different classes of receptors on their surface that play multiple roles in platelet function. (See, e.g., Saboor, M. et al., Platelet receptors; an instrumental of platelet physiology, Pak. J. Med. Sci., 29 (3): 891-896 (May-June 2013)). The number of receptors, the distribution of the classes, and the overall function of the receptors all play a role in overall platelet function (with GPIIb/IIIa, GPIb, P2Y12, TP and PAR 1/2 are GPVI the most relevant) that is affected by blood flow and reactant delivery to the platelet at the site of binding. Coagulation is driven by a multitude of cofactors, many of which are delivered to (and removed from) the site of coagulation by way of blood flow (and subsequent diffusion into and through the clot). These coagulation factors can also be affected by genetic variability and overall concentration in the blood (as many are produced in the liver), and are mediated by many types of drugs, food, nutrients/vitamins, and hormones, to name a few. Therefore, the interaction of platelets and coagulation factors at the site of clotting is dynamic, and directly affected by diffusion which is impacted by blood flow, and distribution/concentration of blood components (such as fibrinogen).

Hemodynamics can also affect hemostasis; platelets in particular are affected significantly by blood flow dynamics. Platelets are approximately 1-3 microns in size in comparison to biconcave red blood cells (RBC) which are roughly 7-8 microns in diameter. Platelet function is influenced by a fluid dynamic process where RBCs concentrate towards the center of a vessel (in flowing blood) and exclude platelets from that volume, pushing them outwards and enriching their concentration in a "cell free layer" close to the vessel walls. (See, e.g., Sugihara-Seki, M. et al., Margination of Platelet-Sized Particles in the Red Blood Cell Suspension Flow through Square Microchannels, Micromachines, 12, 1175 (2021) (doi.org/10.3390/mi12101175). This specifically increases platelet interaction with vessel walls (or device microfluidic channel surfaces). Therefore, a device that can also provide basic blood measures of hematocrit and platelet count (as well as other measures) would be greatly beneficial to understanding the performance of the assay in regard to platelet and fibrin signals. The system discussed herein could provide such measures by way of spectroscopic analysis of the blood in the fluidic paths, using published methods for determining hematocrit, oxy/deoxyhemoglobin and even platelet counts. (See, e.g., Lipowsky, H. et al., Hematocrit determination in small bore tubes by differential spectrophotometry, Microvascular Research, Vol. 24 (1), p. 42-55 (1982); Mattley, Y. et al., Light scattering and absorption model for the quantitative interpretation of human blood platelet spectral data, Photochem Photobiol., Vol. 71 (5), p. 610-619 (2000); Kitamura, Y. et al., Spectrophotometric determination of platelet counts in platelet-rich plasma, International Journal of Implant Dentistry, Vol. 4 (29) (2018)).

Devices and Methods to Derive Platelet and Fibrin Signals

In general, blood can be flowed over a reaction zone at initial wall shear rates that are physiologic. This ranges widely based upon vessel diameter and blood pressure, but in general ranges from 100 to 500 seconds$^{-1}$ for venous blood flow to 500 and much higher s$^{-1}$ for arterial blood flows. With stronger wall shear forces, different biological parameters are involved. For example, platelet binding in high arterial shear is directly impacted by von Willebrand Factor (vWF) that has little to no effects at venous shear.

Since vWF is a key component of hemostasis, and known diseases affect vWF function, then an assay's sensitivity toward such factors can be "tuned" by changing the assays operating shear rate. While vessel diameters range widely (from 1 cm for large arteries to microns for capillaries), there are practical limits to what can be achieved from an assay perspective in terms of creating a physiologically representative model of hemostasis. Too small and the assay easily occludes from particulate debris, is difficult to manufacture, and/or generates significant backpressure. Too large and the amount of blood needed for an assay is impractical. For a typical blood draw, 0.1-3 mL of blood is common and does not inconvenience the patient in any way. This translates into a flow device that has small vasculature-like paths, on the order of tens to a few hundred microns in cross-section.

In some embodiments, the pathways in the device can be substantially cylindrical to match the vasculature in the body. However, while vasculature in the body is approximately cylindrical, this shape may be difficult to manufacture precisely in a microfluidic device. Instead, in some embodiments, platelet and fibrin behavior for blood flow through high aspect ratio rectangular paths approximates plane Poiseuille flow through infinite parallel plates. With flow paths of this size, 500 uL of blood can provide up to 15 minutes or more of clot formation time, which is more than sufficient to analyze platelet and fibrin behavior. The clot zone of the device can be a multitude of sizes, from only a few microns wide to millimeters in length. From a practical standpoint, a clotting zone of, e.g., 100-500 microns inclusive, 100-450 microns inclusive, 100-400 microns inclusive, 100-350 microns inclusive, 100-300 microns inclusive, 100-250 microns inclusive, 100-200 microns inclusive, 100-150 microns inclusive, 150-500 microns inclusive, 200-500 microns inclusive, 250-500 microns inclusive, 300-500 microns inclusive, 350-500 microns inclusive, 400-500 microns inclusive, 450-500 microns inclusive, 100 microns, 150 microns, 200 microns, 250 microns, 300 microns, 350 microns, 400 microns, 450 microns, 500 microns, or the like, allows for sufficient signal to accumulate over a 15 minute assay period. The clotting zone could be applied to all sides of the flow path (top, bottom, left, right), but can generate fully occlusive clots when applied to only one side of a geometric flow path (e.g. rectangular). Therefore, in some embodiments, the clotting zone can be applied to, e.g., the top side of the flow path, the bottom side of the flow path, the left side of the flow path, the right side of the flow path, combinations thereof, or the like. While rectangular flow paths are practical to produce, alternative flow path cross sectional shapes (e.g. semi-circular) are also contemplated. The clotting zone could include one reaction site, or could include multiple reaction sites within the same flow, and in proximity to one another. Detection of the accumulation of platelets and fibrin can be accomplished optically (e.g. direct fluorescence), or with any number of additional methods available to anyone skilled in the art.

In some embodiments, a device could include passivation of the flow paths/fluidics surfaces in order to avoid activation or inadvertent reactions with the blood sample. In other embodiments, surface modification of the flow paths/fluidics could include modification of the surface to more mimic the in vivo characteristics of the body (e.g., coating the surfaces with a fatty acid to mimic cellular membranes, or to literally grow epithelial cells within the device to form pseudo tissue like flow paths).

Platelet and Fibrin Detection

To determine the state of platelet and fibrin function, a platelet label and fibrin label are applied to the blood sample being processed. This permits the simultaneous detection of platelets and fibrin at the same clotting zone of the device. This of course does not prevent one from using either label independently if desired, (or additional labels) but to evaluate both fibrin function and platelet function together, both labels are applied to the same sample at the same time. Only a brief incubation (on the order of seconds) is required to label platelets, and no incubation time is required for fibrinogen. A platelet label, for example, could be an antibody to human CD61 (a platelet integrin) that is conjugated with Alexa 488. A fibrin label, for example, could be human fibrinogen conjugated with Alex 594. The fibrinogen-594 is added to the blood sample as a small proportion of the existing native fibrinogen, which is then incorporated into the forming clot as a proportion of total fibrin. Alternative detection methods are anticipated that utilize the basic functional biochemistry of clot formation. $\alpha$2-antiplasmin (A2-APF) is a protein that impedes fibrinolysis, and is naturally cross-linked to fibrin during clot formation. (See, e.g., Liu, Y et al., Fluorescent peptide for detecting factor XIIIa activity and fibrin in whole blood clots forming under flow, Res. Pract. Thromb. Haemost., 7; 8 (1): 102291 (December 2023), doi: 10.1016/j.rpth.2023.102291, PMID: 38222077, PMCID: PMC10787300). Fluorescently labeled A2-APF will incorporate into the growing clot coincident with fibrin, providing an additional means to monitor fibrin formation. Other detection moieties could be used instead of fibrinogen-594, such as the moieties discussed in International Patent Application No. PCT/US2024/014159, which is incorporated by reference.

In some instances, plasma, instead of whole blood, may be useful to analyze. While plasma lacks the cellular components of whole blood, additions to the plasma, such as viscosity modifiers, freeze dried red blood cells, freeze dried platelets, microparticles, and other blood components could be added to create a material that could be analyzed by the device. In some instances, the blood (or plasma) sample may be pre-treated with chemicals to avoid complications of platelet function and coagulation, caused by the collection and handling of blood, such as contact activation. For example, Corn Trypsin Inhibitor (CTI) is a small protein that is localized in the kernels of most species of corn. CTI is not only an inhibitor of trypsin, but is also a specific human factor XIIa inhibitor. The inhibitor forms a one-to-one complex with either trypsin or factor XIIa, and when added to blood or plasma, prolongs the activated partial thromboplastin time without affecting the PT assay. The specificity for factor XIIa makes the inhibitor useful for the segregation and study of tissue factor (TF) dependent coagulation reactions. The use of CTI to study TF-dependent reactions has been documented in the literature. (See, e.g., Rand, M. D. et al., Blood clotting in minimally altered whole blood, Blood, Vol. 88 (9), p. 3432-3445 (1996); Cawthern, K M. et al., Blood coagulation in hemophilia A and hemophilia C, Blood, Vol 91 (12), p. 4581-4592 (1998); Dargaud, Y. et al., Platelet-dependent thrombography: a method for diagnostic laboratories, British Journal of Hematology, Vol. 134 (3), p. 323-325 (2006); Mann, K. G. et al., Citrate anticoagulation and the dynamics of thrombin generation, Journal of Thrombosis and Hemostasis, Vol. 5 (10), p. 2055-2061 (2007)).

Studies indicate that suppression of the contact pathway of coagulation may be essential when attempting to perform TF-dependent assays in whole blood or plasma samples. The addition of CTI at the point of sample collection prevents activation of the contact pathway during subsequent sample processing steps, thus reducing in vitro artifacts. The most common use of CTI is associated with thrombin generation assays when attempting to work at low TF concentrations. Additional chemicals can be used for the purpose of modifying blood and plasma behavior, prior to, and during use within a device. A common example of such a chemical is chloromethylketone (FPRCK (Phe-Pro-Arg-chloromethylketone; commonly referred to as PPACK), which is a rapid thrombin inhibitor and EGRCK (Glu-Gly-Arg-chloromethylketone; commonly referred to as GGACK), which is a rapid factor Xa inhibitor. Both FPRCK and EGRCK are used extensively during protein isolation procedures to inhibit serine protease activity and prevent further conversion of zymogens to active enzymes.

FIG. 13 shows various envisioned configurations of the exemplary device flow paths. It should be understood that the flow paths illustrated in FIG. 13 can be used in independent/separate devices, or multiple flow paths can be incorporated into a single device with any combination of single or multiple clot sites with the same or differing TF concentrations. Single or combined devices can utilize any combination of clot size and TF concentrations. In some embodiments, the flow path can include a single reaction chamber, and single independent flow path. (see FIG. 13, flow paths 1-3). For example, flow path 1 in FIG. 13 includes one independent flow path with one small clot site, and one TF concentration. Flow path 2 of FIG. 13 includes two independent flow paths with one large clot site, and one TF concentration. Flow path 3 of FIG. 13 includes three independent flow paths with three small clot sites, and one TF concentration. In some embodiments, the flow path can utilize more than one concentration of TF. For example, flow path 4 of FIG. 13 includes one independent flow path with clot sites having different TF concentrations located serially.

In other embodiments, a flow path can have more than one flow path, with independent reactions. (See FIG. 13, flow paths 5-6) Flow path 5 of FIG. 13 includes two separate paths and two different TF concentrations in parallel. Flow path 6 of FIG. 13 includes two separate paths with two reaction zones on separate planes (z-axis), with two different non-overlapping (z-axis) sites having different TF concentrations in parallel. Each flow path represented in FIG. 13 includes a reaction chamber fluidically connected to a reaction zone via a flow path, the reaction zone having one or more clot sites. The clot sites can have the same TF concentration or different TF concentrations. A flow path leads from the reaction zone to waste. Flow path 5 of FIG. 13 includes two separate, parallel flow paths with clot sites in an overlapping position, with the reaction zone on the same plane (along the z-axis). Flow path 6 of FIG. 13 includes two separate, parallel flow paths with clot sites in a non-overlapping configuration, with the reaction zone on different planes (along the z-axis).

In some embodiments, the independent flow paths can be connected to a common sample entry point to simplify the addition of a blood sample. In some embodiments, this common entry point can also include a common reagent chamber to facilitate the interaction of the blood sample with reagents common to all reactions (e.g., CTI, fibrin label, platelet label, combinations thereof, or the like). In some embodiments, each independent flow path can contain an independent reagent and/or mixing chamber where reagents unique to each flow path can be added, stored and/or mixed with the blood sample. In some embodiments, the flow paths can coincidently be connected to a priming circuit whereby pressure applied to the priming circuit can push fluid into the flow paths of the device, providing blocking of surfaces and elimination of air (which avoids bubble entrapment). A blood sample to be tested can first be mixed with CTI, then labeled with platelet label and fluorescent fibrinogen in a sample chamber, and mixed with specific drugs or reagents in the same or additional reagent/mixing chambers. This mixture can then be drawn through the device (under vacuum or pressure) and across the reaction zone. A single clotting site can provide both a platelet signal and a fibrin signal.

More than one reaction zone or clotting site can be included in the device to provide averaging of the platelet and fibrin signals. (see, e.g., FIG. 13). The clotting site can be of different sizes to facilitate a more or less reactive surface area. A single flow path, for example, can be split into two or more independent clotting sites with independent or convergent exits. In some embodiments, a device can include independent flow paths and clotting sites on different layers of the device, creating a multi-dimensional flow path (in the x, y and z planes).

FIG. 14 shows additional diagrammatic representation of exemplary microfluidic device configurations. Pressure can be applied at the inlet to push blood through the device, vacuum can be applied at the exit to pull the blood through the device, or a combination of pressure and vacuum can be applied to move/oscillate blood back and forth through the device. The device can include a blood entry chamber (in some embodiments including CTI) that acts as an inlet for blood. The blood entry chamber is fluidically connected by flow paths to a sample chamber. Each device or flow path includes a reagent and mixing zone disposed upstream of a reaction zone having a clot site. One or more clot sites can exist in the reaction zone. Downstream of the reaction zone, the device/system includes a prime pump configured to apply a positive pressure to the flow path. Each flow path can be independent and leads to waste downstream, which optionally can be under a negative pressure (vacuum). As a non-limiting example, the device of FIG. 14 can have the patient's neat blood, the patient's blood with the drug Andexxa, the patient's blood with the drug Praxbind, and the patient's blood with excess drug, rivaroxaban, with reagents located in the reagents and mixing zone.

FIGS. 15 and 16 show additional diagrammatic representations of exemplary microfluidic device pathway configurations. In particular, FIG. 15 is a diagrammatic view of a microfluidic device pathway including a multi-layer structure with two unique reaction zones, and FIG. 16 is a diagrammatic view of microfluidic device pathway including a single-layer structure with two unique reaction zones. Although it is technically possible to have two reaction zones within the same pathway, there may be technical difficulties this can create (e.g., upstream vs. downstream reactive zones conflicting one another). The flow paths of FIGS. 15 and 16 can provide parallel paths in three or two dimensions to allow for multiple reaction zones within the same device. For example, the device of FIG. 15 includes a layer 300 with a flow path 302 and a reaction zone 304, and a vertically offset layer 306 with a flow path 308 and a reaction zone 310. The three-dimensional configuration allows for two reaction zones offset in the z-axis direction on separate planes. As a further example, the device of FIG. 16 includes a single layer 320 with flow paths 322, 324 spaced in a two-dimensional manner, each flow path 322, 324 including its respective reaction zone 326, 328.

Multi-Level Drug Sensitivity: While fluidic devices can be made with a single reaction zone with a specific level of reactivity to platelet function and coagulation, it may be advantageous to have devices with more than one reaction zone with each reaction zone at a different level of reactivity. For example, Tissue Factor (TF) is the primary activator of the process of coagulation whereby a given amount of TF, bound within the reaction zone, will produce a specific coagulation response for any given sample. Collagen concentration can equally be modified to differing levels to modify the behavior of platelet binding and activation. This means that creating a second reaction zone with a differing level of TF and/or collagen will naturally produce a different level of reactivity to a given sample. This is useful, for example, when attempting to detect a drug which inhibits one or more reactions in the coagulation cascade. Different levels of tissue factor in the reaction zone will cause different rates of generation of the molecular targets of certain anticoagulants, which can then modulate the apparent activity of a given dose of drug. In the case of DOACs, two TF concentrations could be chosen such that one TF concentration in the reaction zone would be sensitive to a low level of DOAC drug, (e.g. <100 ng/ml or <50 ng/mL) while a second TF concentration in a second reaction zone would be more sensitive to a moderate to high dose of DOAC drug, (>100 ng/mL or >200 ng/ml. This is useful, for example, at resolving limitations in assay linearity or sensitivity where reaction kinetics at a given TF concentration may simply not result in measurable differences between similar drug levels. By having two distinct reaction zones with differing TF concentration, linearity or sensitivity can be maintained across a wide range of biologically relevant drug concentrations.

Multiple reaction zones within the same device can be utilized to provide varying degrees of reactivity to different biological scenarios, such as differing drug levels. For example, these different reaction zones can be placed sequentially within the same blood flow, in parallel within the same plane, where the same blood sample is split between two separate paths each crossing a unique reaction zone, or even dimensionally separated where one flow path/reaction zone is placed upon a separate fluidic layer in comparison to the first, all within the same device. (See FIGS. 13 and 15).

In its simplest embodiments, a device can include a single reaction chamber, and single independent flow path. A blood sample to be tested would be labeled with platelet label and fluorescent fibrinogen in a reaction chamber inside the device (or reaction tube outside the device). This mixture is then drawn through the device (under vacuum or pressure) and across the reaction zone. A single clotting site would provide both platelet and fibrin signal. More than one reaction zone or clotting site can be included to provide averaging of the platelet and fibrin signal. A single flow path for example could be split into two or more independent clotting sites with independent or convergent exits.

The method provides rapid and more precise hemostasis testing (as compared to traditional systems), especially during the critical 10-20 minute patient triage window, and can be used to improve early bleeding risk assessment, stabilization, and care transition, while driving evidence based transfusions, blood product utilization, and costly drug reversals. The method provides results that can be used by medical professionals to reduce overall costs of patient care, while adhering to existing industry quality and patient safety guidelines.

In accordance with embodiments of the present disclosure, an exemplary system for platelet and fibrin detection and quantification is provided. The system includes a first inlet port configured to receive a fluid sample. In some embodiments, the system can include more than one inlet ports, e.g., 4 or 8 inlet ports, or the like. The system includes an outlet port, and microfluidic flow paths fluidly connecting the inlet port with the outlet port. In some embodiments, the system can include more than one outlet ports, e.g., 1, 4 or 8 outlet ports, outlet ports equal to inlet ports, outlet ports not equal to inlet ports, or the like.

The unmodified sample can be labeled on or off device, before use. The labeling consists of a platelet specific label, and a fibrin specific label. Introduction of the labeled sample into the inlet port allows for the generation of a fibrin and platelet signal when the sample is flowed over the reaction zone. The fluid sample can be, e.g., a raw blood sample, a citrated blood sample that is recalcified, a heparinized blood sample that is treated with protamine, or the like.

The system can include a processing instrument configured to manipulate the sample within the device and coincidently monitor a direct response of the fluid sample to identify platelet and fibrin function. In some embodiments, the instrument can include a light source for monitoring clot development in the microfluidic flow paths. A green fluorescent signal can indicate platelet formation as the clot develops, a red fluorescent signal can indicate fibrin formation as the clot develops. The processing instrument can be configured to measure the fluorescent intensity of the monitored clots as they develop, and can be configured to correlate the measured fluorescent intensity with platelet and fibrin accumulation in the microfluidic flow paths. The processing instrument can be configured to compare the fibrin signal to the coincident platelet signals for all reactions to determine relative platelet and fibrin function in the fluid sample.

In some embodiments, the assay device can include a separate priming port to pre-fill the device, or the priming could be accomplished by way of the outlet port. The method includes generating fibrin and platelet signal for each of the inlet ports. The method includes identifying the overall state of coagulation and platelet function from the unmodified sample.

The method can include imparting a light source onto the microfluidic flow paths to monitor clot development in the microfluidic flow paths. The method can include the instrument receiving as input at a processing device a measured fluorescent intensity of the monitored clot development. The method can include correlating the measured fluorescent intensity with platelet and fibrin accumulation in the microfluidic flow paths, using the instrument.

The system includes an optical instrument with computing capability, and an assay device capable of receiving a biological sample and further capable of receiving one or more chemical reagents. Introduction of the biological sample and the one or more chemical reagents into the assay device results in a biological process by which fibrin and platelets accumulate at a reaction zone of the assay device. The system includes a fluorescent assembly capable of detecting the biological process by way of fluorescent labeling, and detection of a resulting accumulating fluorescent signal. The fibrin and platelets accumulated at the reaction zone of the assay device, and the accumulating fluorescent signal are usable to determine at least one of a platelet function, fibrin function and level of "normalcy", in comparison to a healthy normal population.

In some embodiments, the system can be used for monitoring the effect of any type of drug that affects platelet and fibrin behavior, and can thereby be used to determine drug effect within the biological sample.

In some embodiments, the assay device can include one or more inlet ports, each configured to receive the biological sample. The biological sample is an unmodified sample including a platelet specific label and a fibrin specific label.

The assay device can include an outlet port, and microfluidic flow paths fluidically connecting each of the inlet ports with the outlet port. As used herein, the term "fluidically" or "fluidic" refers to a communication that has static or active fluid communication along the ports. As used herein, the term "active" flow or fluid communication refers to flow that is brought about by pressure or vacuum applied directly or indirectly to the fluidics of the device. The introduction of the biological sample into the inlet ports generates a fibrin signal and a coincident platelet signal.

At least one of the inlet ports can be configured to receive a drug that can modify platelet or fibrin signal (increase or decrease). The drug could antagonize or attenuate the activity of platelets or fibrin formation, either directly or indirectly. In some embodiments, the system can be used to determine effective dosing for a patient by allowing one to determine when a patient is reduced to some percent of platelet or fibrin formation function as a target.

In some embodiments, the method can include identifying an overall state of coagulation from the unmodified sample by evaluating the fibrin signal. For example, the method can include receiving a concentration of the drug to a point which produces no further attenuation of the fibrin signal to obtain the drug concentration at which there is fully attenuated fibrin signal.

In some embodiments, the method can include generating a platelet signal coincident with the fibrin signal. Any combination and/or permutation of embodiments is envisioned. Other objects and features will become apparent from the following detailed description considered in conjunction with the accompanying drawings. It is to be understood, however, that the drawings are designed as an illustration only and not as a definition of the limits of the present disclosure.

In accordance with embodiments of the present disclosure, an exemplary system for detecting and quantifying platelet and coagulation function within a biological sample is provided. The system includes a detection instrument with computing capability. The system includes an assay device capable of receiving a biological sample. Introduction of the biological sample into the assay device results in a biological process by which fibrin and platelets may accumulate at a reaction zone of the assay device. The assay device is capable of receiving one or more chemical reagents compatible with the biological sample, and usable for detecting the accumulation of the fibrin and platelets within the reaction zone. The fibrin and platelets, and their associated signals, accumulated at the reaction zone of the assay device are usable to determine at least one of a platelet function, a coagulation function, a platelet normalcy, a fibrin normalcy, a platelet response to a drug, or a coagulation response to a drug, within the biological sample.

The system can include a fluorescent assembly capable of detecting the biological process by way of fluorescent labeling. The system can include a processing device configured to receive as input a measurement of the accumulating platelet and fibrin signal, and the processing device is configured to correlate a measured fluorescent intensity with the accumulation of platelets and fibrin in microfluidic flow paths of the assay device, to determine at least one of a platelet function, a coagulation function, a platelet normalcy, a fibrin normalcy, a platelet response to a drug, and/or a coagulation response to a drug, within the biological sample. In some embodiments, the one or more chemical reagents can be a fluorescent reagent capable of labeling the fibrin and platelets from the biological sample that results in a fluorescent assembly that reports the accumulation of the fibrin and platelets. The system can include a light source for monitoring the accumulation of platelets and fibrin within microfluidic flow paths of the assay device, and for detecting a reaction to the one or more chemical reagents or response to one or more drugs.

The assay device can include an inlet port configured to receive the biological sample, wherein the biological sample is an unmodified sample including a platelet specific fluorescent label and a fibrin specific fluorescent label. The assay device can include an outlet port, and microfluidic flow paths fluidically connecting the inlet port with the outlet port. The passage of the biological sample through the microfluidic flowpaths can generate a platelet signal and a fibrin signal.

In some embodiments, the biological sample can include a whole blood sample, a processed blood sample, a blood sample treated with an anticoagulant, a blood sample treated with a reagent to prevent intrinsic pathway coagulation activation, a citrated blood sample that is recalcified, a heparinized blood sample treated with protamine, or a blood sample treated with an antiplatelet drug to reduce platelet activation.

The assay device is capable of receiving one or more drug reagents compatible with the biological sample that may modify the accumulation of the platelets and fibrin within the reaction zone. The system can include a processing device configured to compare the biological sample platelet and fibrin signals to a healthy population platelet and fibrin signals, respectively, or a diseased population platelet and fibrin signals, respectively, or a targeted population platelet and fibrin signals respectively, to determine a difference in platelet and fibrin activity in comparison to population data.

A platelet signal and a fibrin signal can be compared independently or dependently to each other or the population data, over time or at fixed points in time, or in comparison to one or more thresholds in fluorescent signal, or time. The system can include a processing device configured to collect the population data for comparison to the biological sample platelet and fibrin signals. The system can include a processing device configured to use population statistics, mathematical characteristics, and statistical methodologies of the population data to evaluate the biological sample platelet and fibrin signals in comparison to the population data. The population statistics, the mathematical characteristics, and the statistical methodologies are used to determine at least one of percent platelet function, percent fibrin function, or categorical determination of normalcy in unmodified and modified samples. The system can include a processing device configured to monitor a patient over time, in the presence of drugs that affect platelet and fibrin function.

In accordance with embodiments of the present disclosure, an exemplary method for platelet and coagulation function detection and quantification is provided. The method includes adding a biological sample to an assay device, and adding one or more chemical reagents to the assay device to generate a biological process by which fibrin and platelets may accumulate at a reaction zone of the assay device. The method includes detecting the biological process with a fluorescent assembly by way of fluorescent labeling and detection of a resulting accumulating fluorescent signal. The method includes using the fibrin and platelets accumulated at the reaction zone of the assay device, and the accumulating fluorescent signal, to determine at least one of a platelet function, a coagulation function, a platelet normalcy, a fibrin normalcy, a platelet response to a drug, or a coagulation response to a drug, within the biological sample. In some embodiments, the method can include adding one or more drugs to the biological sample to effect a change to platelet and/or fibrin function.

BRIEF DESCRIPTION OF THE DRAWINGS

To assist those of skill in the art in making and using the system for coagulation and platelet function related data collection and analysis, reference is made to the accompanying figures, wherein:

FIG. 5 an example of fibrin and platelet classification by standard deviation ranges;

FIGS. 6A-6C are published tables on normal ranges for common blood tests;

FIG. 7 is an example display of fibrin data by box plot;

(FIG. 17A), showing platelet signal at 21° C. (FIG. 17B), showing fibrin signal at 37° C. (FIG. 17C), and showing fibrin signal at 21° C. (FIG. 17D).

FIGS. 21A-12B are graphs showing "normal" fibrin function (FIG. 21A) and platelet function (FIG. 21B), with corresponding statistics and standard deviation ranges as collected on the device of FIGS. 18A-18B;

DETAILED DESCRIPTION

The system and method for platelet and coagulation function data collection and analysis provides a rapid and precise assessment of a patient's hemostatic function in a testing environment that is analogous to the blood clotting physiology found in the human body. The system performs a hemostasis assay that can be read from a portable tabletop instrument (analyzer) with an integrated computer, preformatted disposable cartridge and associated software. The system can be used to determine early risk stratification, targeted treatment, and patient monitoring. The assay can mimic the microenvironment of blood clot formation, and incorporates hemodynamic flow and discrete clot activation. The system can provide real-time (or substantially real-time) characterization of blood clotting physiology under flow. The system can provide dynamic, multiplexed signaling of platelets and fibrin in a single test. The system can provide functional response to drug levels. The system can provide rapid results (e.g., over the course of 15 minutes or less) in real-time or substantially real-time, and provides a comprehensive determination of hemostatic function and drug effects in a single test, within 30 minutes. Such determination can be essential in emergency critical care settings, as well as other patient treatment settings, and assists with drug reversal and monitoring strategies. In addition, the system could provide additional information about clotting behavior, if analyzed over longer periods of time (e.g., fibrinolysis and platelet inhibition, or the like).

The system simulates in vivo conditions and therefore is sensitive to the clotting behavior of the patient. The information and results provided by the system can include independent functional fibrin and platelet response, hemostatic response to drugs, and clotting behavior over time. These results can distinguish platelet and coagulation dysfunction, as well as a drug level associated with a hemostatic dysfunction. The system can facilitate understanding the effects of blood product delivery, e.g., blood transfusion, fresh frozen plasma (FFP), cryoprecipitate, platelets, or the like, as well as real-time monitoring of drug action.

Specific targeting elements at the reaction zone facilitate clotting that involves both platelet accumulation and fibrin formation, coincidently, regardless of the detection reagent.

The combination of the fibrin signal and platelet signal has been shown to be meaningful to determining drug activity. Additional targeting elements can be added to the reaction zone to target additional clotting elements, hemostatic elements, and/or other blood born factors. In some embodiments, clotting can occur in the presence of whole blood that contains all of the necessary components for hemostasis that is a direct reflection of the individual patient's in vivo processes.

Figure 1A:
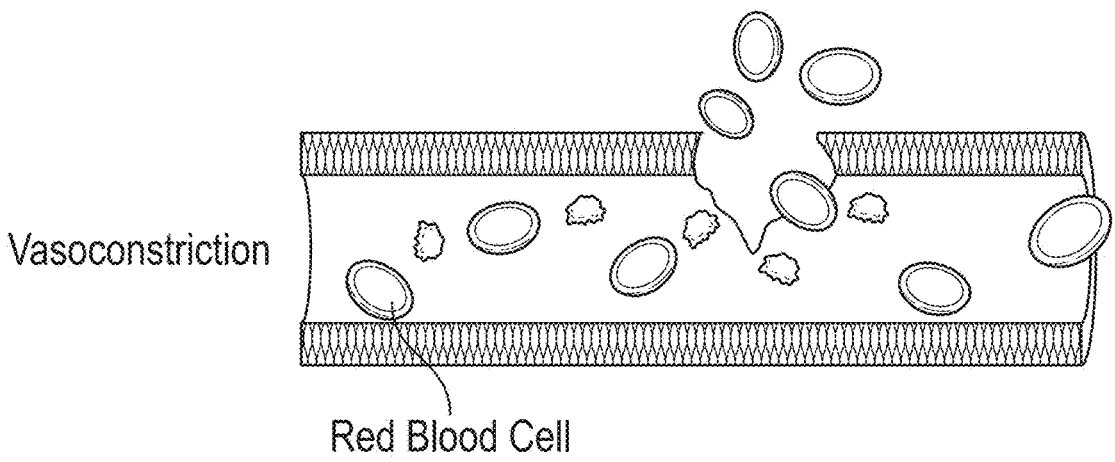
FIG. 1A is a diagrammatic illustration of vasoconstriction with damage exposing collagen and tissue factor.
Figure 1B:
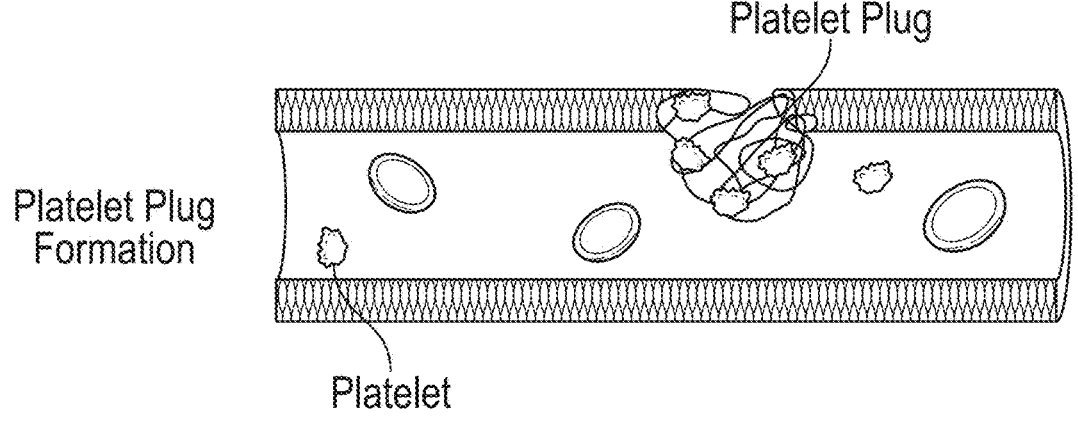
FIG. 1B is a diagrammatic illustration of a platelet plug formation with platelet aggregation.
Figure 1C:
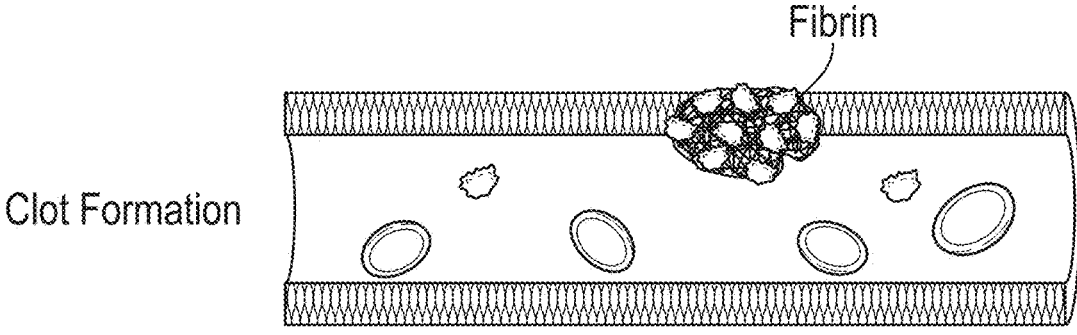
FIG. 1C is a diagrammatic illustration of a clot formation in the form of coagulation.
Figure 2:
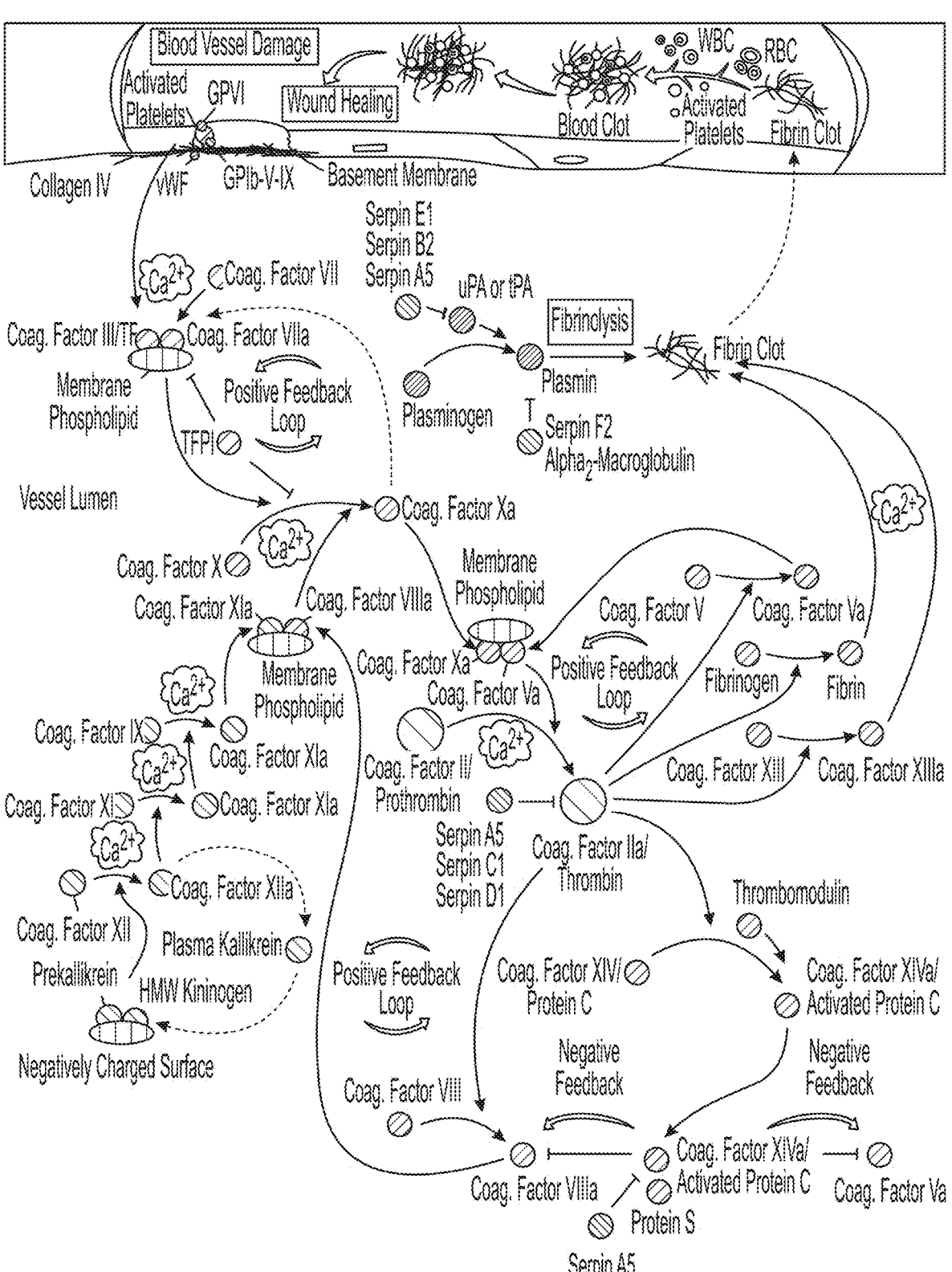
FIG. 2 is a diagrammatic illustration of hemostasis control in the human body.
Figure 3A:
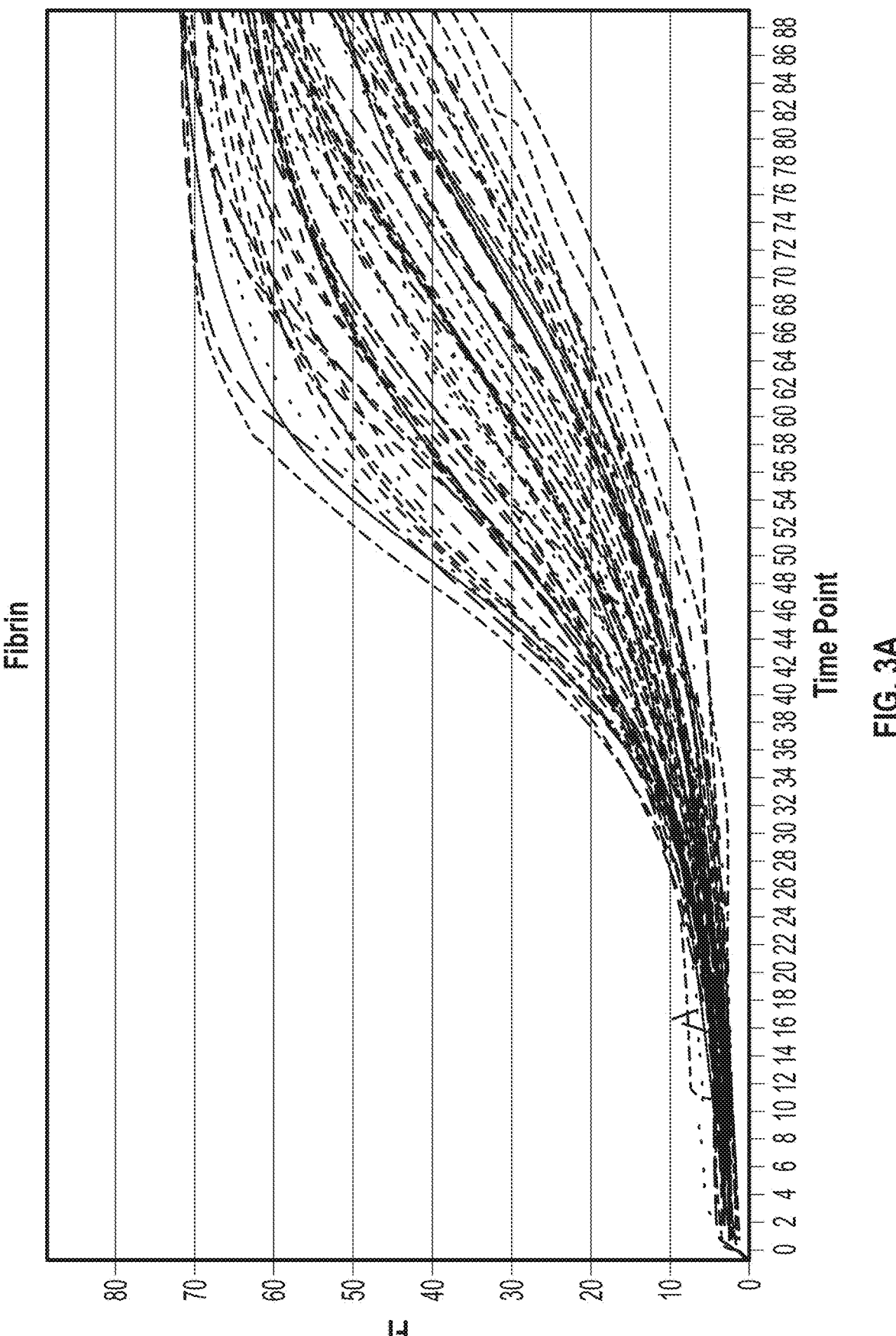
FIGS. 3A-3B are charts of an example of "normal" fibrin function over time (FIG. 3A), and an average fibrin function plot over time (FIG. 3B)
Figure 3B:
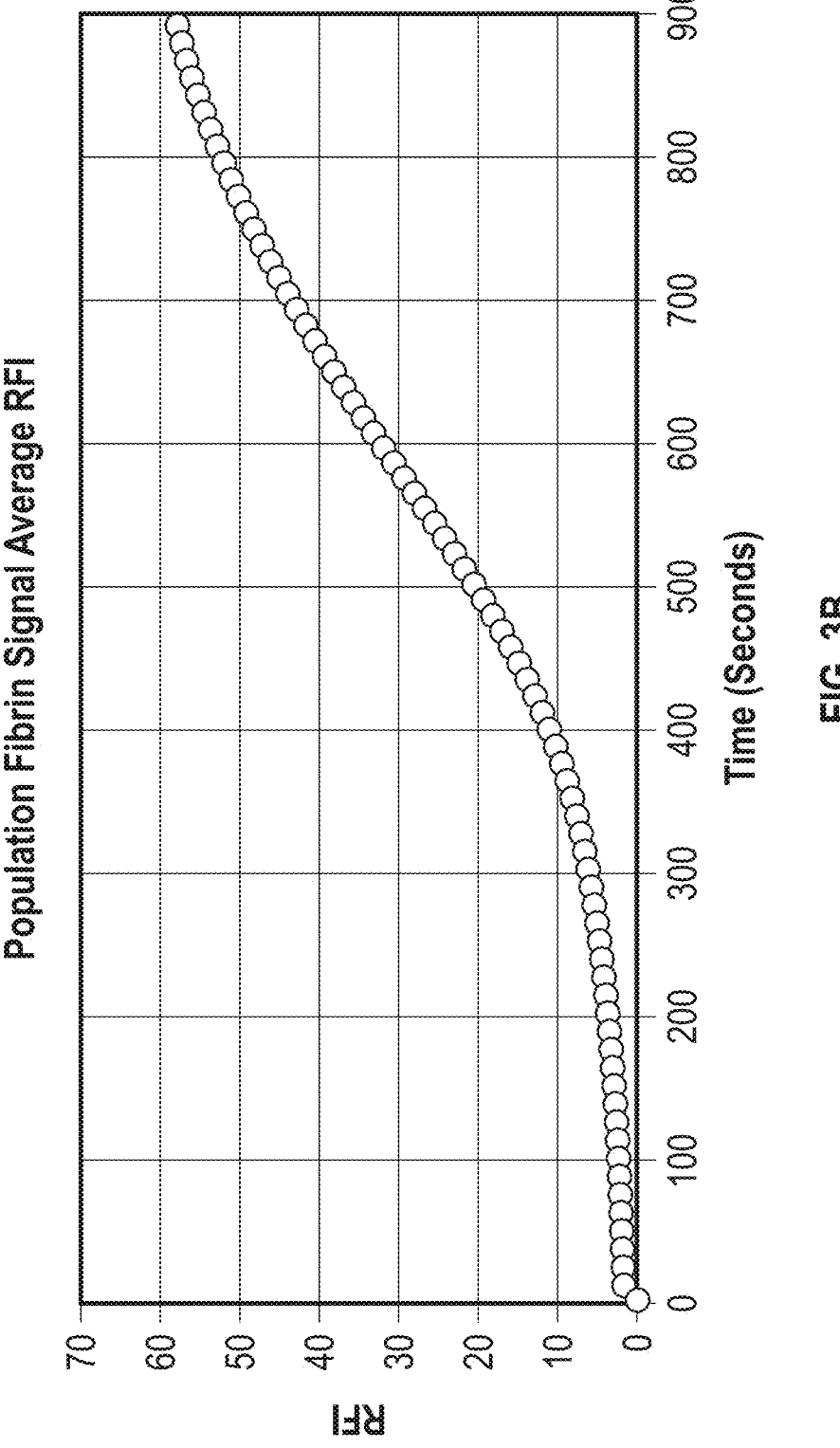
Figure 4A:
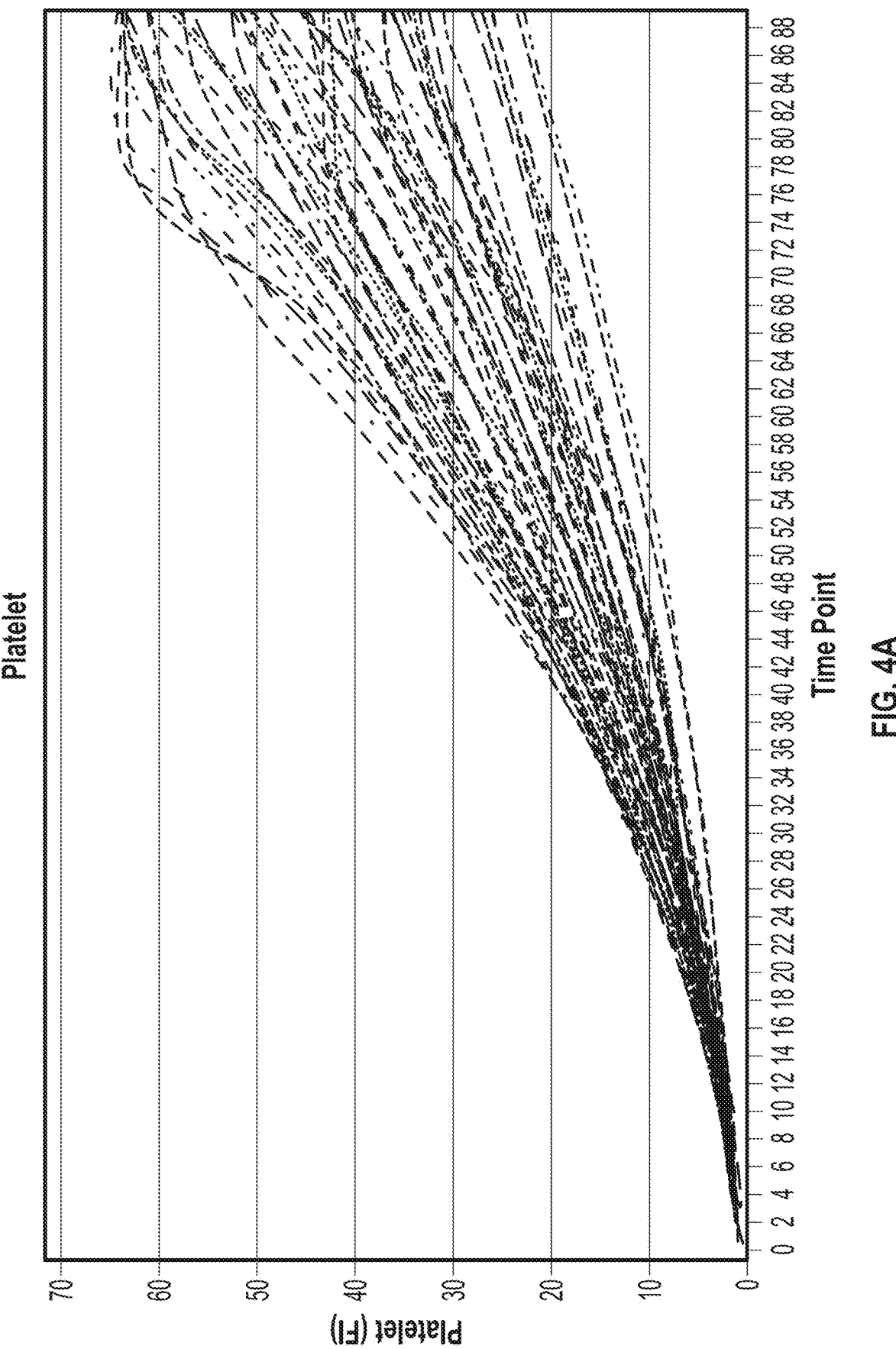
FIGS. 4A-4B are charts of an example of "normal" platelet function over time (FIG. 4A), and an average platelet plot over time (FIG. 4B)
Figure 4B:
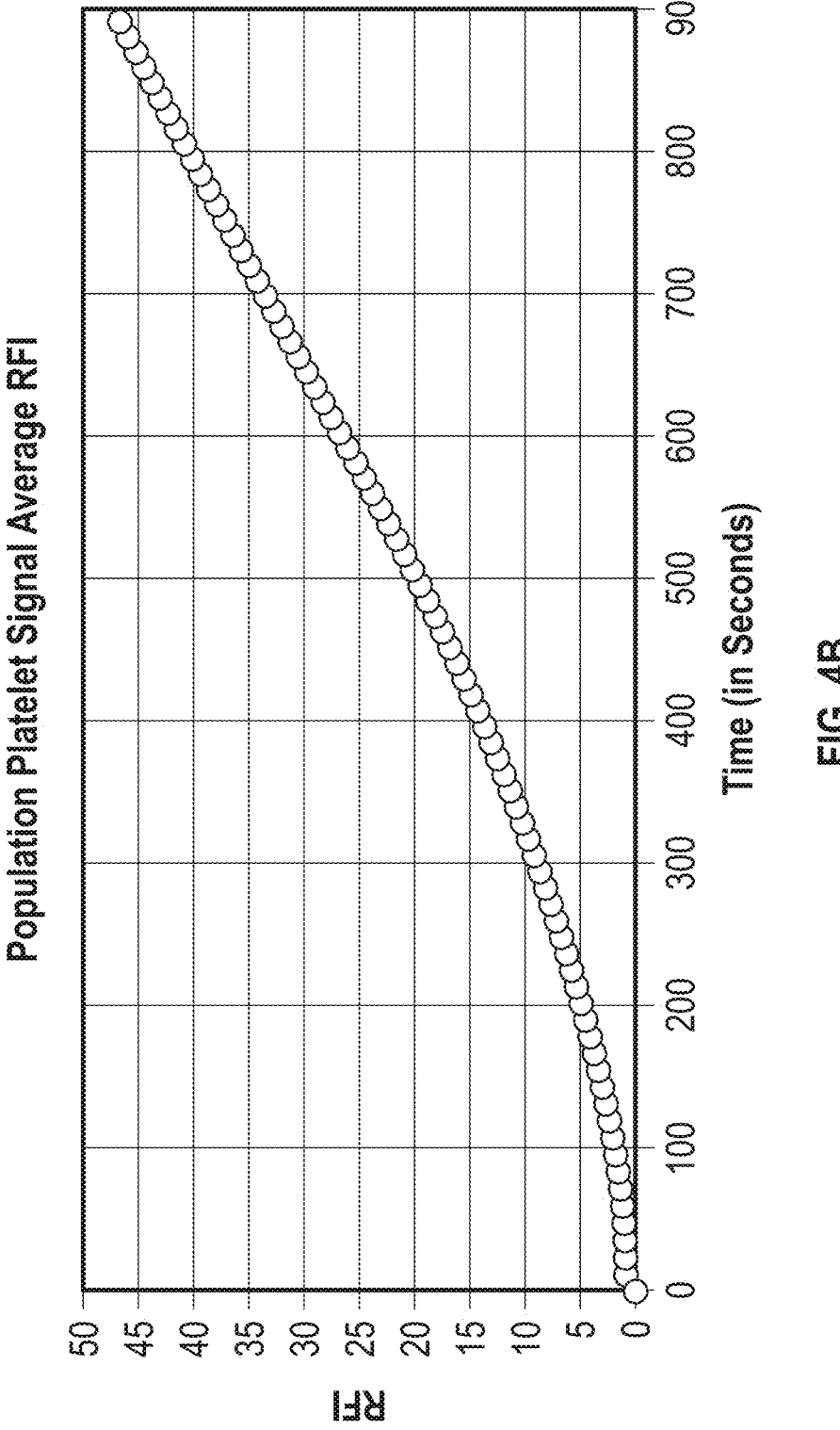
Figure 8A:
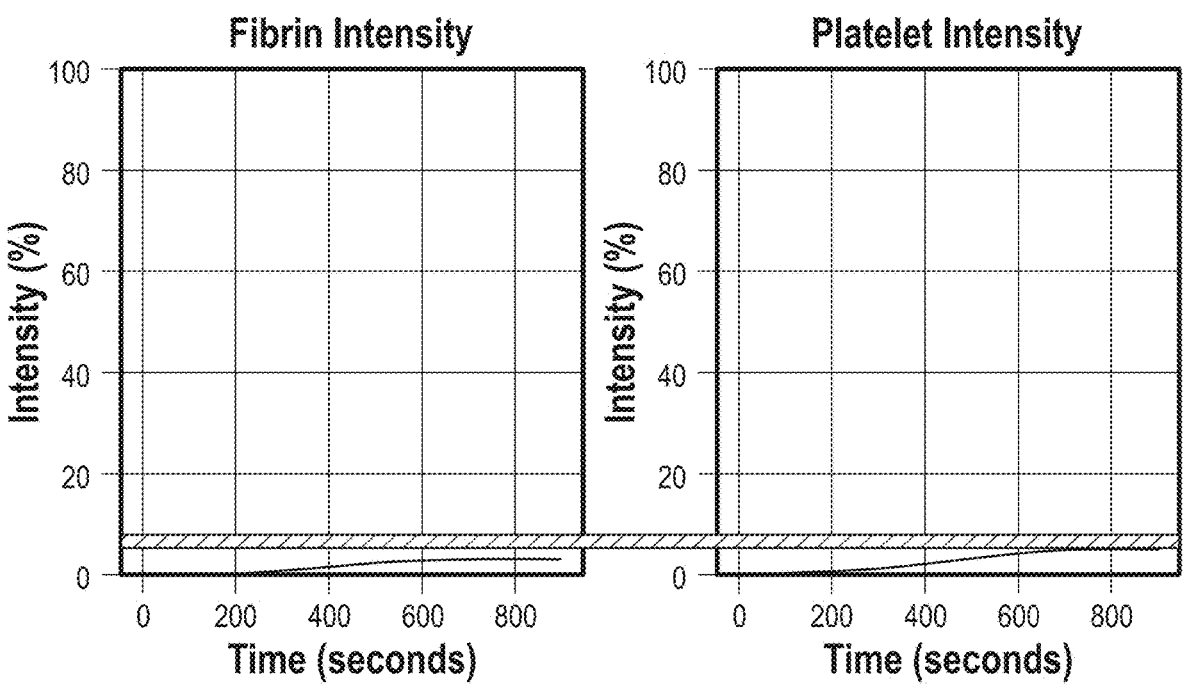
FIGS. 8A-8D are examples of useful assay thresholds, including assay fail warning (FIG. 8A), low platelet warning (FIG. 8B), low fibrin warning (FIG. 8C), and low overall function warning (FIG. 8D)
Figure 8B:
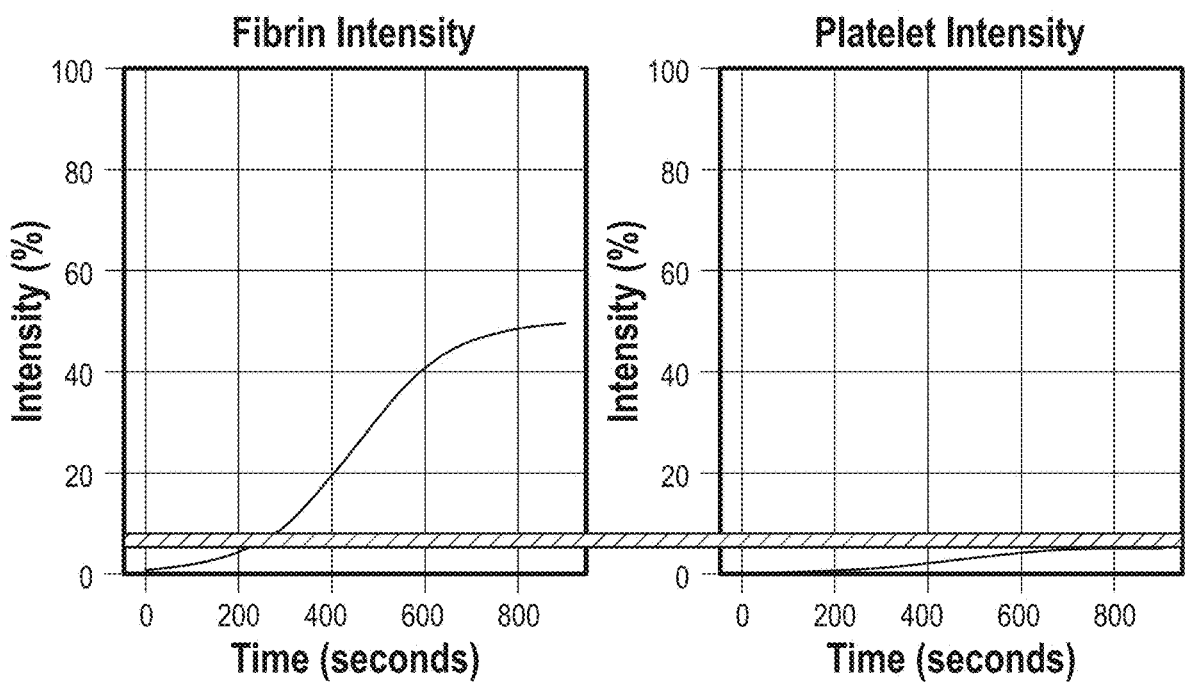
Figure 8C:
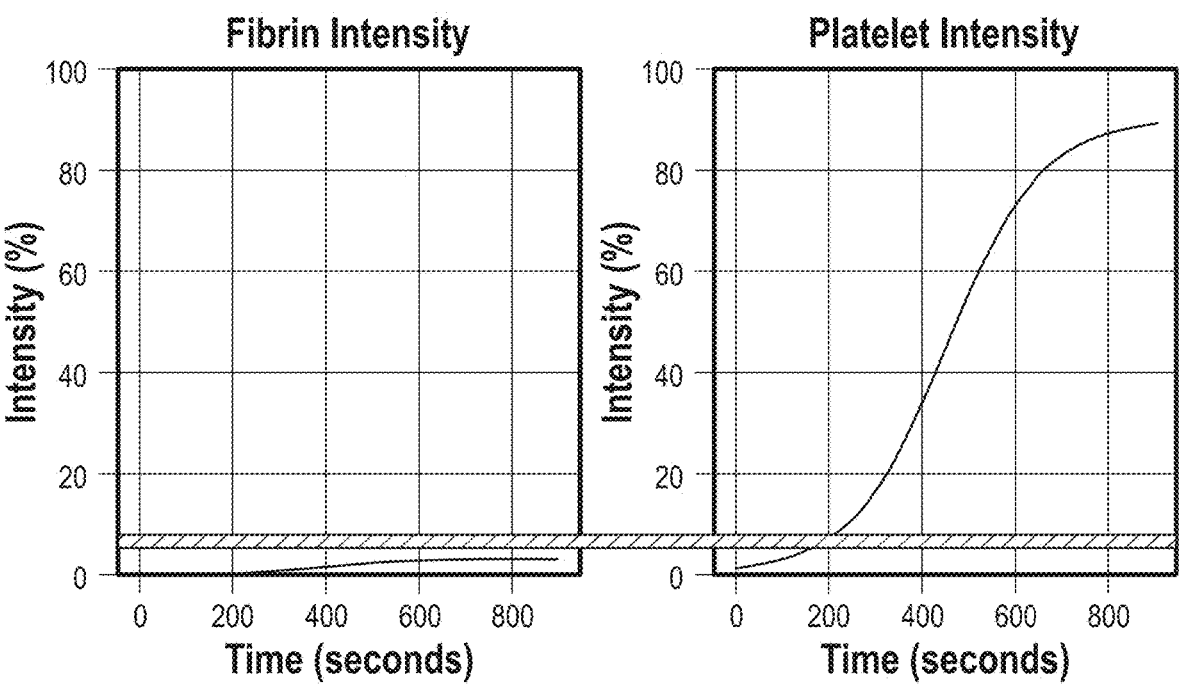
Figure 8D:
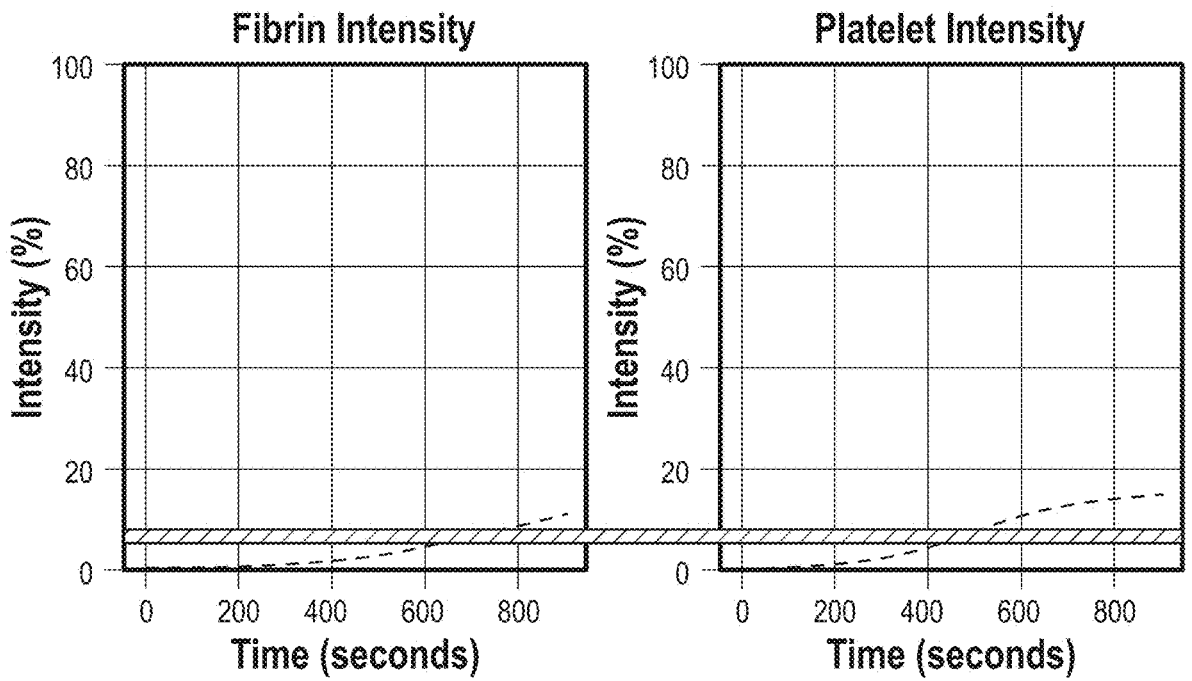
Figures 9A, 9B, 9C:
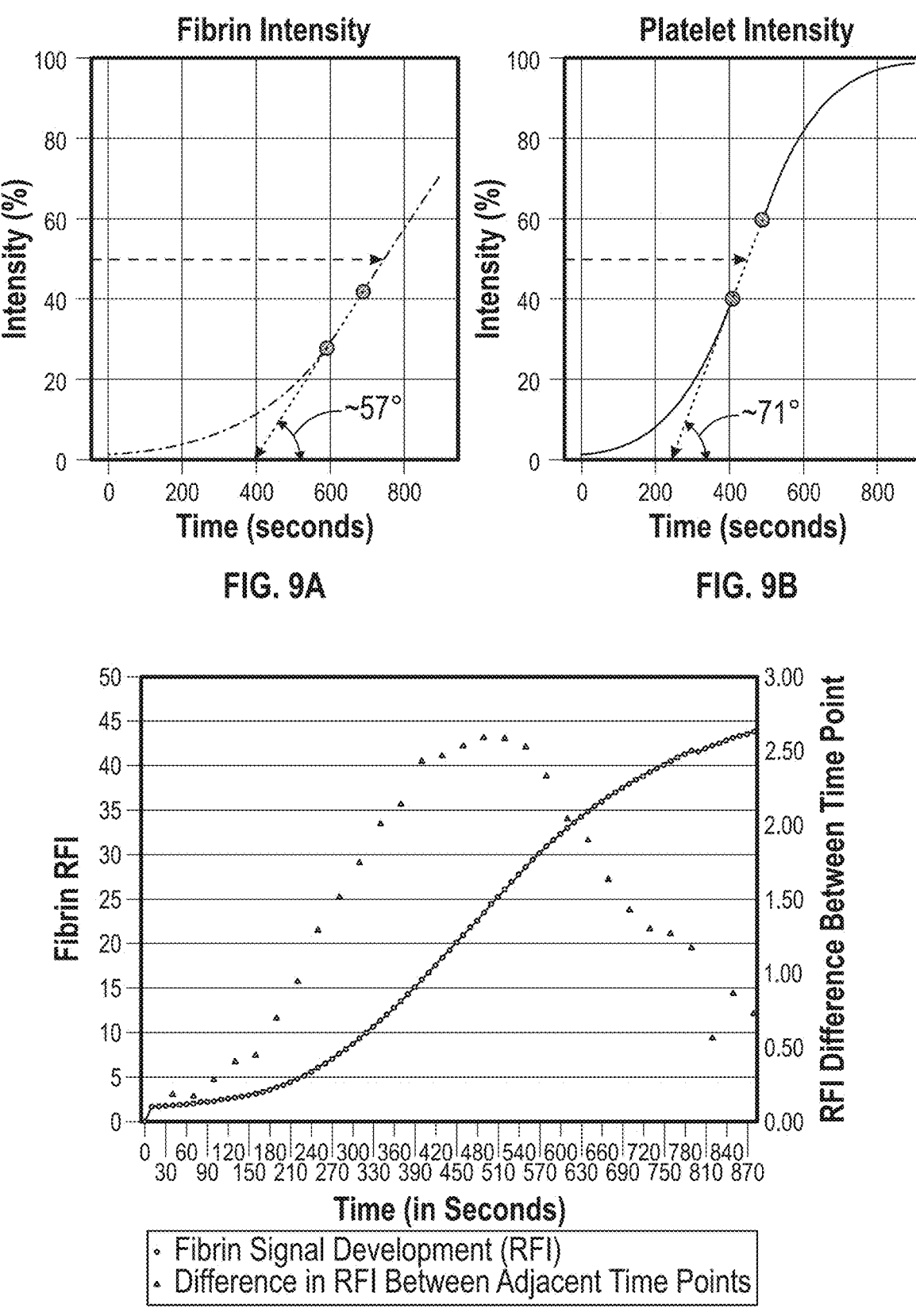
FIGS. 9A-9C are graphs determining RFI signal slope for fibrin intensity (FIG. 9A), platelet intensity (FIG. 9B), change in RFI between time points (FIG. 9C), and derivation of an angle based on change in RFI (FIG. 9D)
Figure 9D:
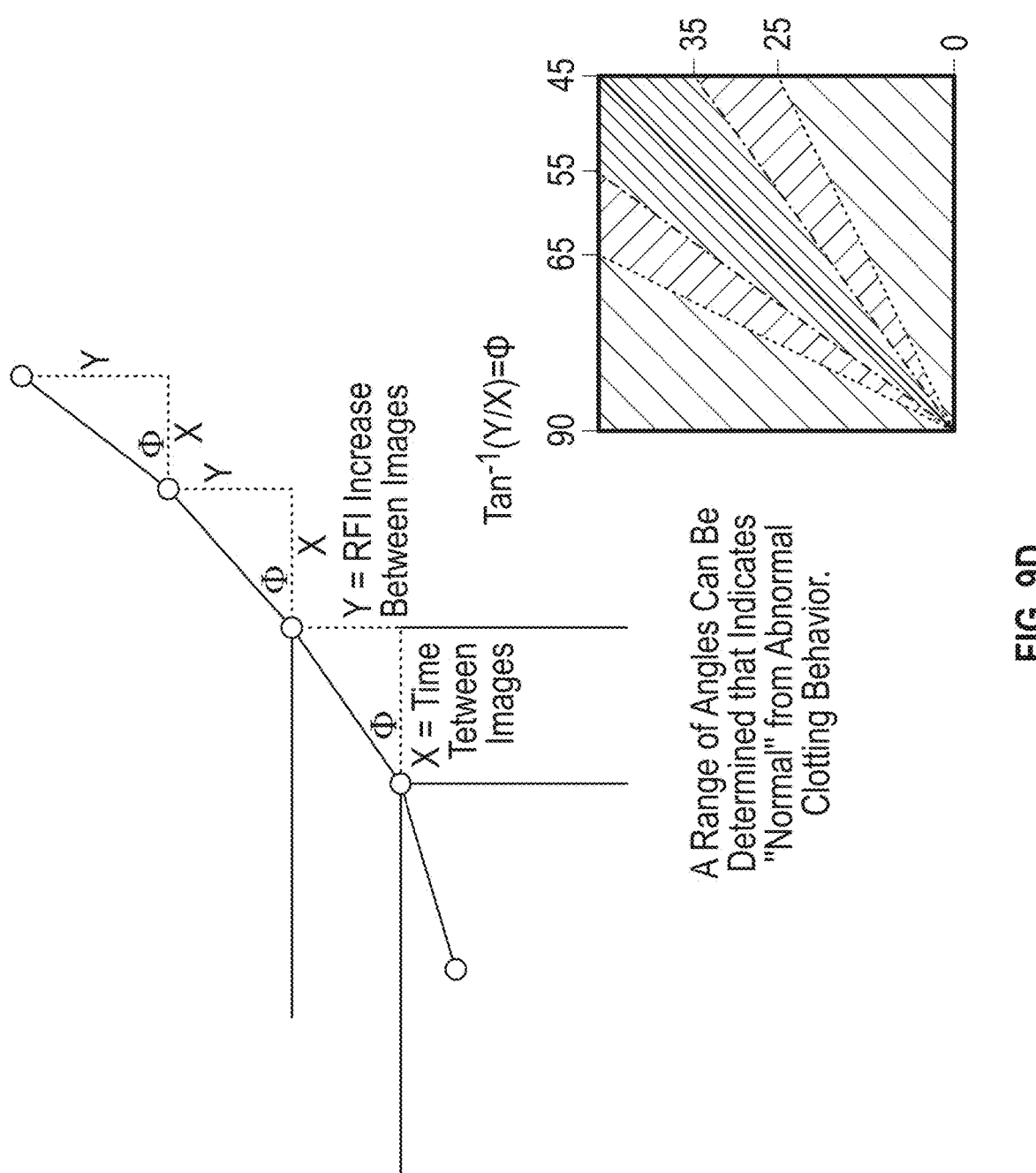
Figure 10:
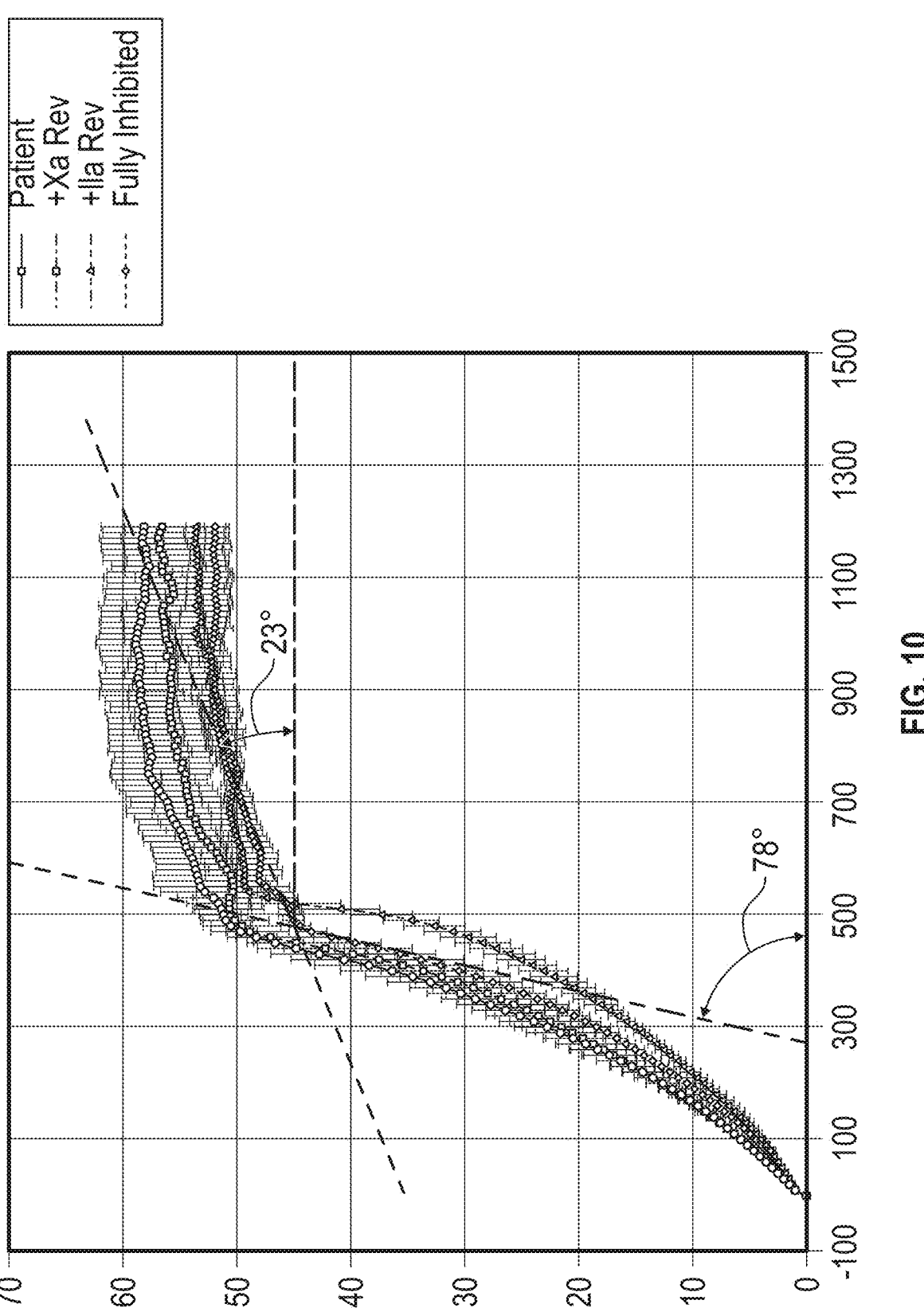
FIG. 10 is a graph demonstrating fluidic occlusion within the flowpaths of the device.
Figure 11:
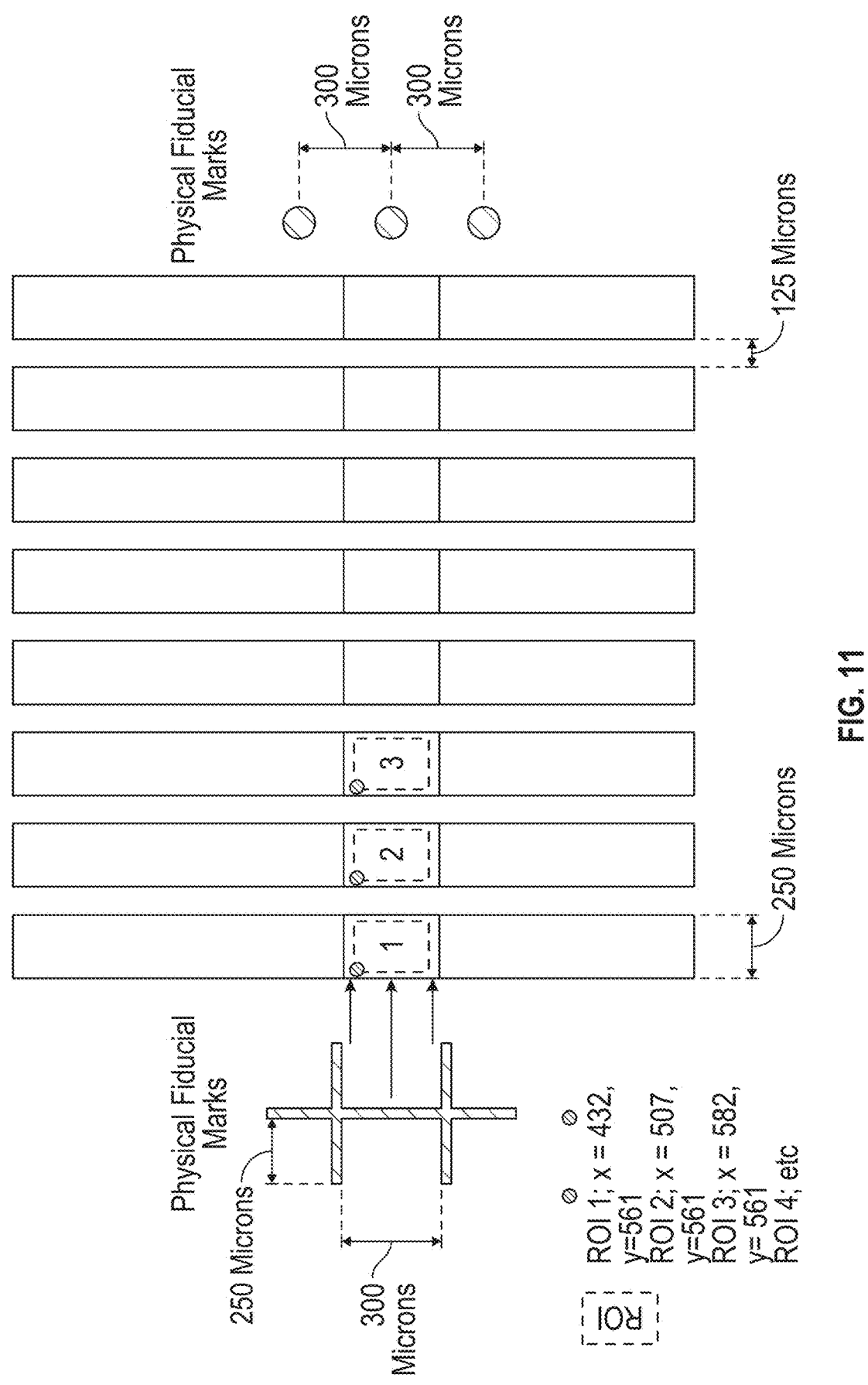
FIG. 11 is a diagram of ROI finding within the flowpaths of the device, including manufacturing fiducials.
Figure 12A:
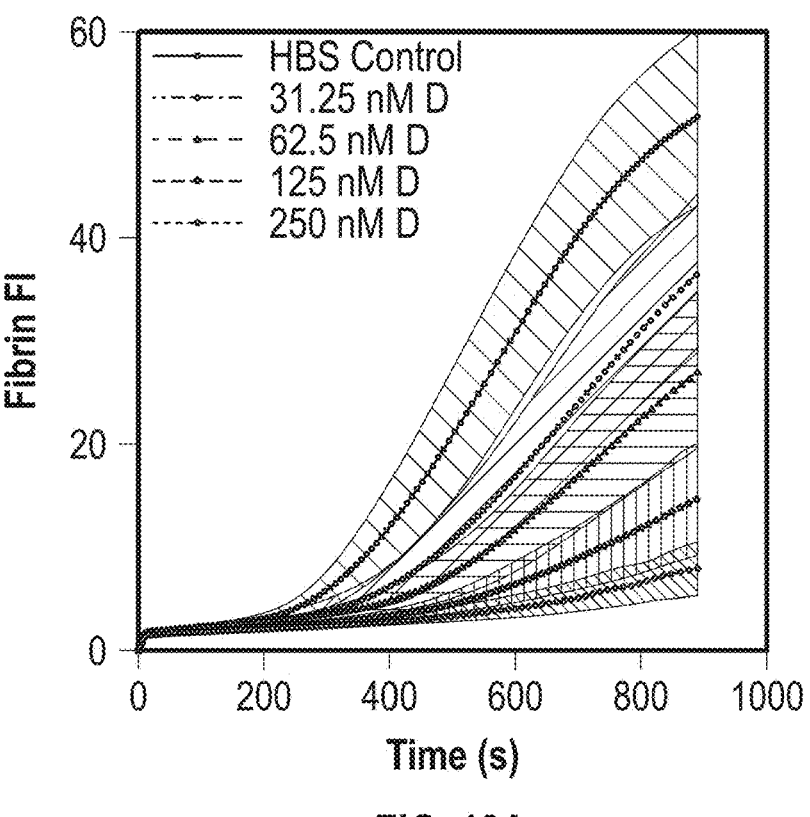
FIGS. 12A-12B are graphs demonstrating the ability to determine drug sensitivity of a blood sample by way of drug spiking of a DOAC drug, dabigatran, for fibrin (FIG. 12A) and platelet (FIG. 12B).
Figure 12B:
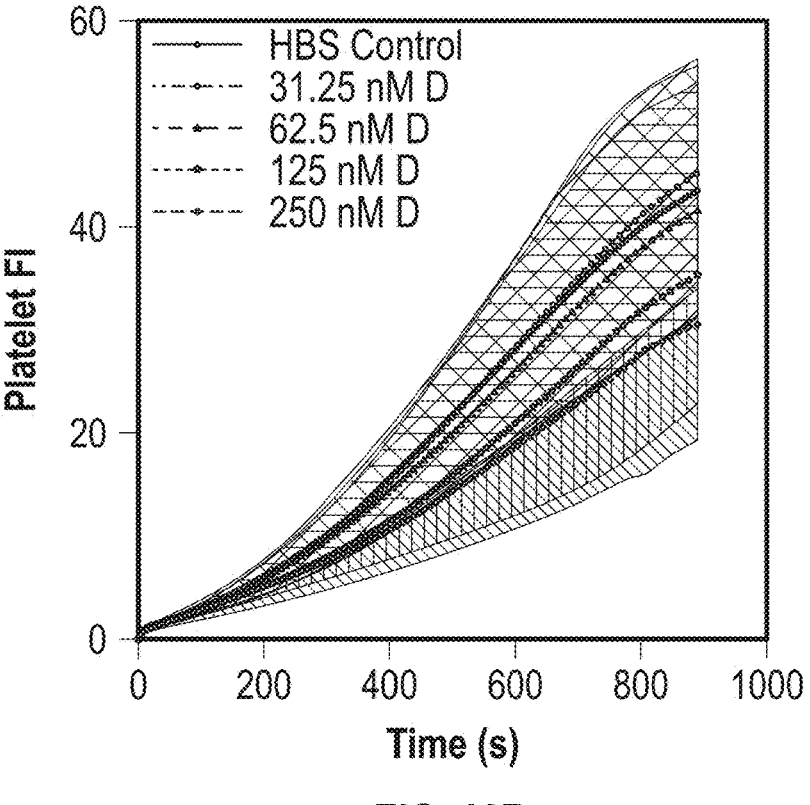
Figure 13:
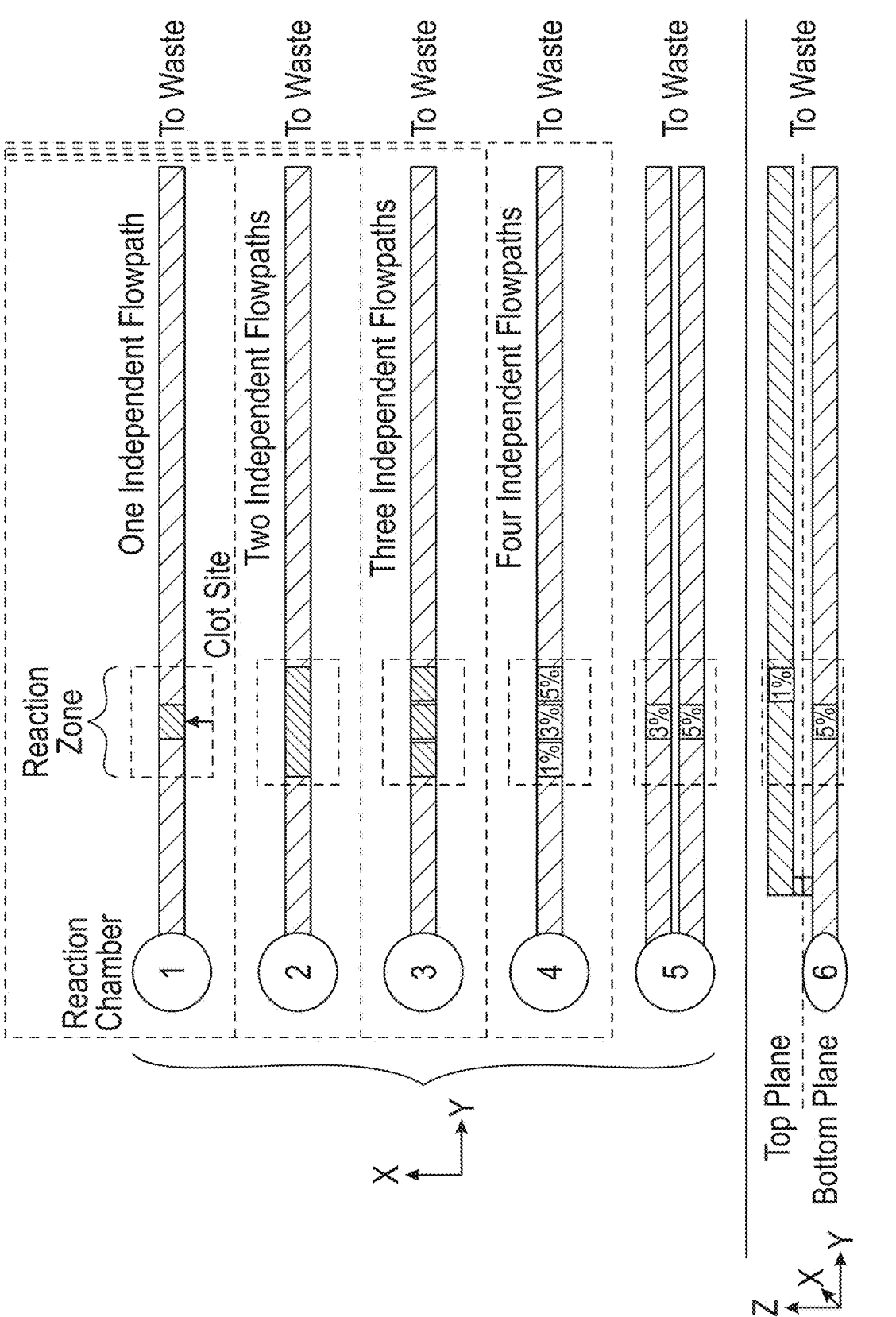
FIG. 13 is a diagrammatic view of microfluidic devices for determining platelet and fibrin function in accordance with embodiments of the present disclosure.
Figure 14:
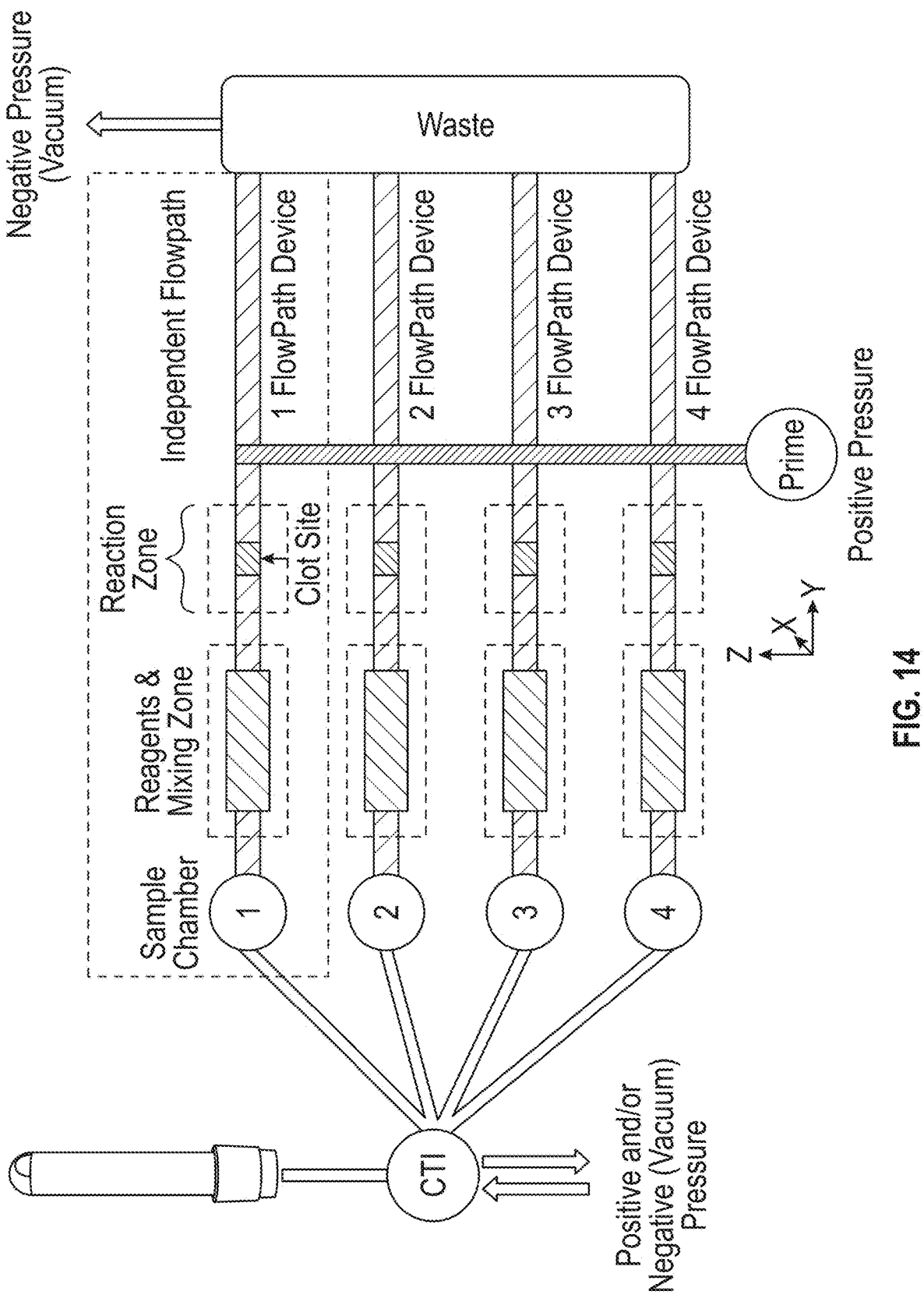
FIG. 14 is a diagrammatic view of microfluidic devices for determining the presence and reactivity of a drug in accordance with embodiments of the present disclosure.
Figures 15, 16:
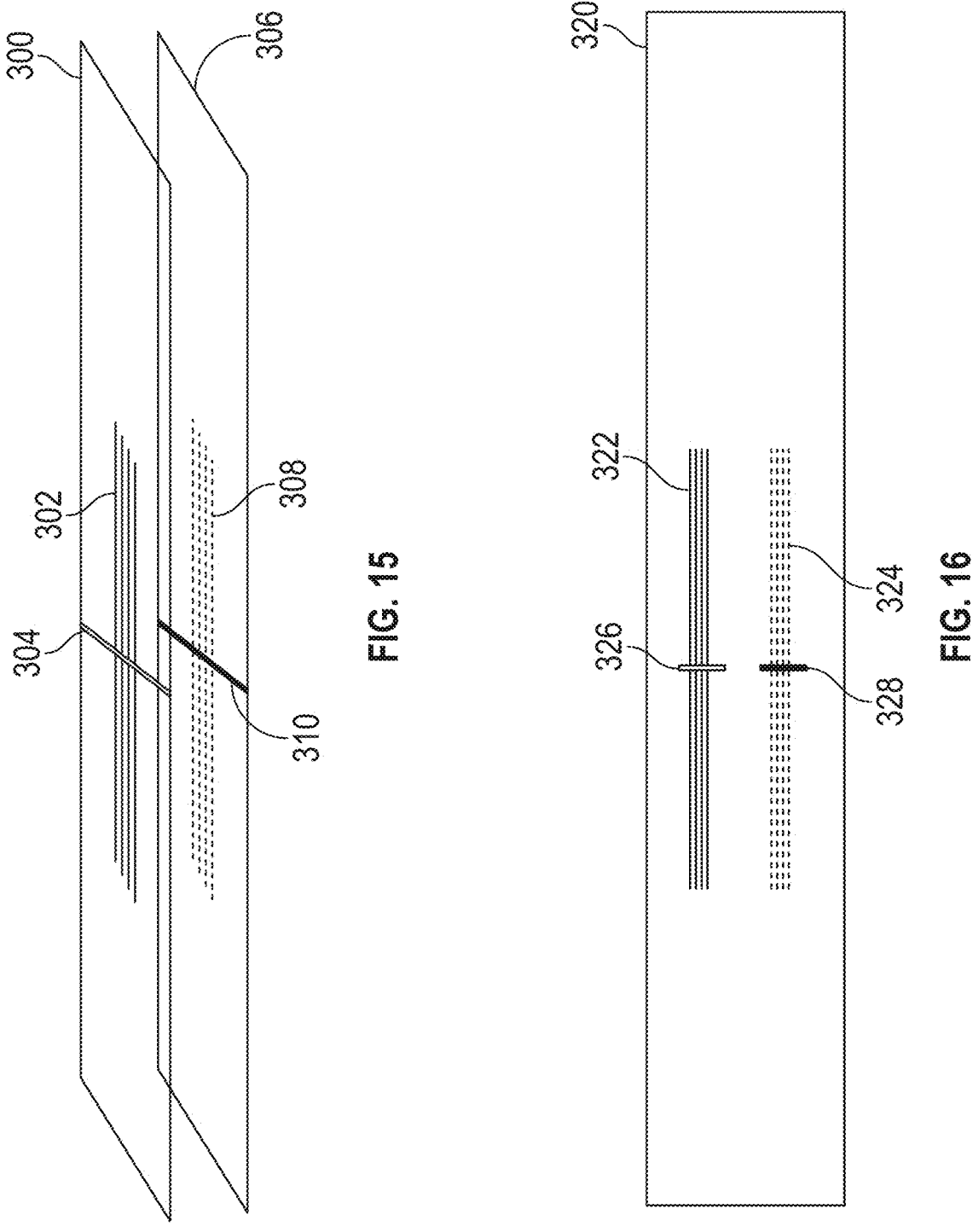
FIG. 15 is a diagrammatic view of a microfluidic device pathway including a multi-layer structure with two unique reaction zones.
FIG. 16 is a diagrammatic view of microfluidic device pathway including a single-layer structure with two unique reaction zones.

In some embodiments, the reaction zone can be "tuned" towards different levels of sensitivity for platelets and fibrin accumulation by varying the specific targeting elements (e.g., collagen, tissue factor) and concentrations, modifying the shear rate, modifying the reaction temperature, or modifying the fluidic dimensions, thereby allowing for specific levels of sensitivity. The reaction zone contains immobilized reagents which bind and activate the platelets and activate coagulation. In some embodiments, more than one reaction zone with more than one level of sensitivity could be placed on the same assay device, thereby broadening the ability of the device to measure a wider range of drugs. (See, e.g., FIG. 13) Blood can be analyzed under physiological flow thereby demonstrating the actual likely behavior of the patient's platelets and coagulation (fibrin) in vivo. In some embodiments, blood flow can be driven through the device by an external source (e.g., a pump) to achieve a specific range of physiological shear conditions. For example, the biological sample flow can be driven within the assay device from the inlet across the reaction zone and to the outlet via application of a pressure gradient using the external source.

Temperature Control and Effects on Assay Results: For a kinetic/time based assay, temperature can play a large role in the behavior of individual blood components (such as the serine protease thrombin). Reactions run at room temperature, some 17 degrees Celsius below body temperature, can have substantially reduced activity (reaction kinetics), as well as increased blood viscosity. A consistent reaction temperature is critical in terms of comparing results across time, location, and sample, to avoid variance caused by differences in the system's environment. While it is possible to analyze blood at lower than body temperatures, the behavior of blood becomes less active the lower the analysis temperature. This can be advantageous to the design of a system that utilizes this effect, as temperature can be used to control or modulate both platelet and coagulation behavior (e.g., reducing or increasing overall signal or rate of signal development, reducing or lengthening the overall assay time and/or modifying assay sensitivity).

The addition of temperature control to the assay can be done most simply through the controlled heating of the system's imaging location. For example, heating elements can be applied to the floor of the imaging area allowing (indirect) convection heat transfer to control the temperature of the space where the fluidic device is being imaged. Enclosing and insulating the imaging/reaction space can provide for reduction in temperature fluctuations. Alternatively, heating elements within the imaging/reaction space can be brought into contact with the bottom of the fluidic device when inserted into the system, to directly heat the device. In some embodiments, a combination of direct and indirect heat transfer can be used. A thermocouple or similar type temperature sensor can be used as a feedback mechanism to control the temperature to a specific setpoint, at, above or below body temperature. In some embodiments, one or more heating elements can be directly applied to, or within, the fluidic device, whereby once placed into the instrument, a connection to the instruments electrical system can supply power to the heating element(s) within the fluidic cartridge. Multiple ways of delivering and applying heat (e.g., direct contact, air, liquid, combinations thereof, or the like) and its control (PID, hysteresis, or the like) to the fluidic device within the instrument are contemplated. In some embodiments, cooling of the imaging/reaction chamber can be applied by means of, e.g., a Peltier device, or the like, to reduce reaction temperatures (and therefore assay activity) if needed.

Applying a consistent temperature to the assay can result in either increased reactivity/signal generally with increasing temperature, and decreased reactivity/signal generally with decreasing temperature. This is advantageous in that sample reactivity, and potentially even sample sensitivity, can be modified simply by way of reaction temperature changes. For example, increasing reaction temperatures can decrease assay time, thereby shortening the length of time to reach a clinical result, which is critical in emergency critical care decision making. Increasing the temperature can increase reaction kinetics for samples that are less reactive. For example, for patients on very high doses of a DOAC drug, the determination of drug concentration can be more precisely discerned if the reaction kinetics are increased by increasing temperature. This can result in improving the assay's sensitivity to higher drug levels; or conversely, making the assay more sensitive to lower drug levels, using lower temperatures. In addition, reducing the temperature can help in evaluating hyper-reactive samples (e.g., hyper coagulation, excessive platelet activity, or the like). Hyper-reactive samples (either coagulation or platelet function) can cause excessive clotting within the device which can lead to fluidic blockage and spurious (or no) assay results. For example, seriously ill (e.g., COVID-19, sepsis, cancer, or the like) patients can present with hyper-coagulation issues. Reducing the reaction temperature of the patient's sample can reduce reaction kinetics sufficiently to avoid early device blockage and allow for useable clinical results.

Figures 17A, 17B:
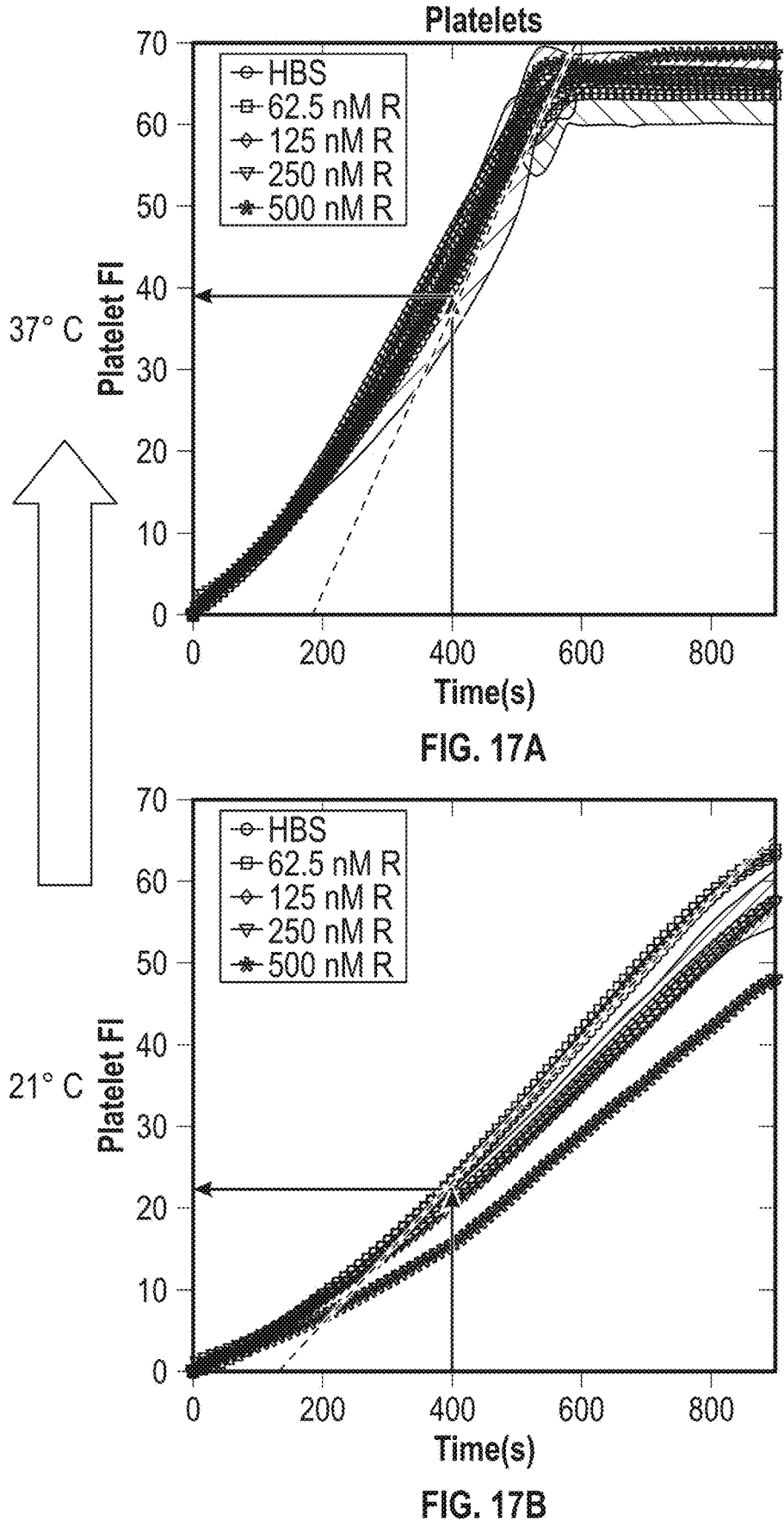
FIGS. 17A-17D are charts demonstrating change in fibrin and platelet signal development in the presence of DOAC at two temperatures, including showing platelet signal at 37° C.
Figures 17C, 17D:
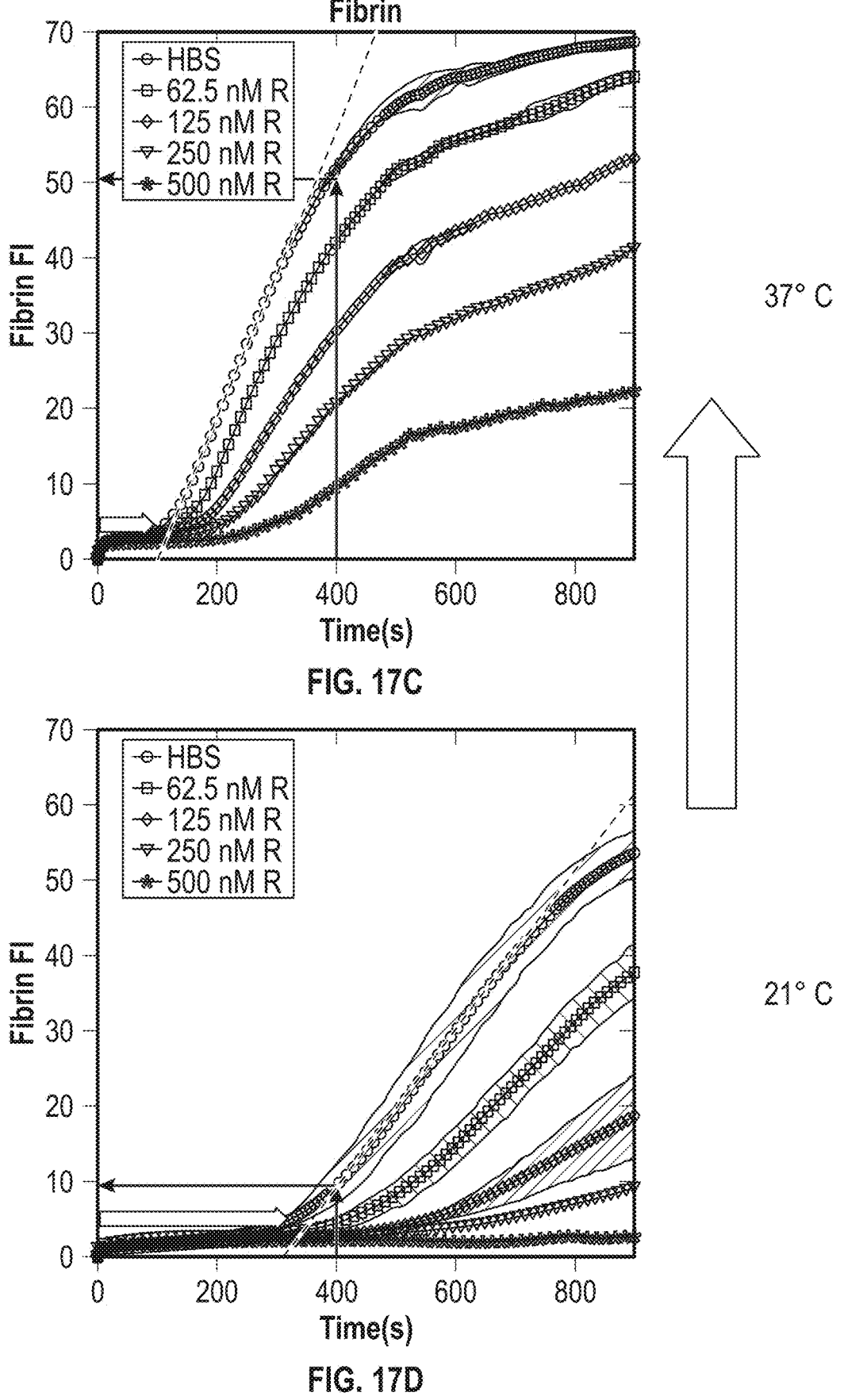

FIGS. 17A-17D demonstrate that in a blood sample treated with different doses of Rivaroxaban, the same overall dose specific fibrin behavior is seen, but with decreased initiation times, increased reaction rates, and higher signal as reaction temperature is increased, relative to body temperature. In particular, FIGS. 17A-17D demonstrate changes in fibrin signal development in the presence of DOAC, at two temperatures. Fibrin signal decreases as Rivaroxaban® dose is increased, in relation to the HBS control, as expected. As temperature increases, fibrin reactions initiate earlier, fibrin and platelet maximum rate of change increases (steeper slope), and fibrin and platelet signals are increased overall at the same point in time. The DOAC drug dose effect seen at higher temperatures follows similar dose behavior seen at lower temperatures. As illustrated in FIGS. 17A-17B, about a two-fold platelet signal increase at 400 s is seen, a substantial increase in maximum rate of change of fluorescence is also seen. As illustrated in FIGS. 17C-17D, about a five-fold fibrin signal increase at 400 s is seen, more than 3× faster initiation, and a substantial increase in rate of signal development is also seen.

The assay device can use flow channels (microfluidics) that mimic physiological structure, size, flow and distribution of cellular and subcellular components, and effect platelet margination under flow. The assay can measure the biological process of hemostasis in real-time, thereby allowing for assessment of the process at all time points during the assay (e.g., a kinetic assay). The system is rapid, providing a clear picture of hemostatic function within 15 minutes (in most cases). The system has a long term possibility of measuring clot lysis, clot strength, hematocrit, and other parameters of interest that affect hemostasis coincidently with platelet and fibrin function.

Figure 18A:
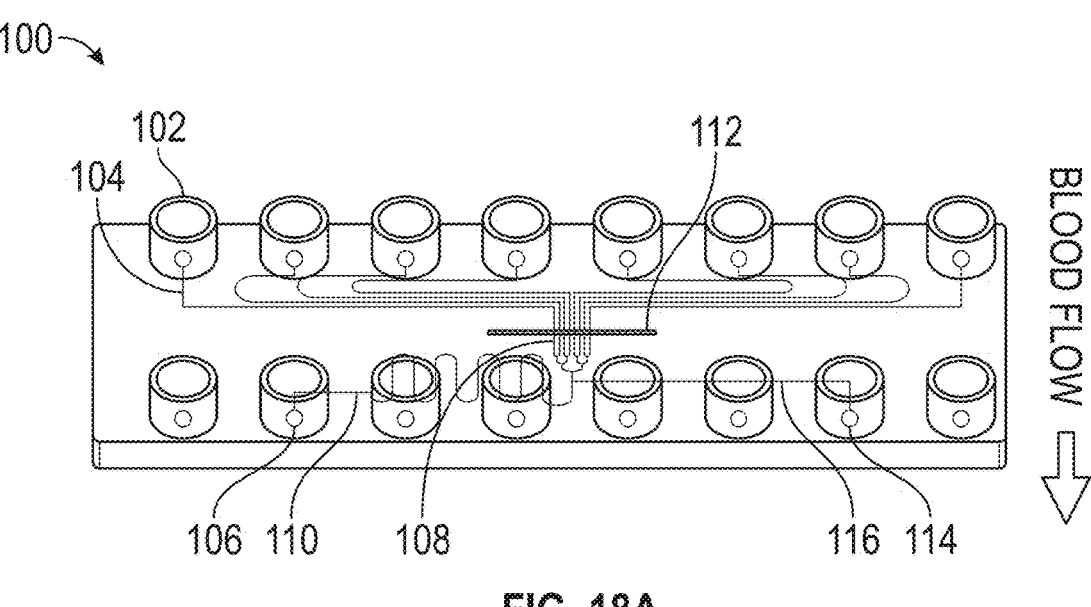
FIGS. 18A-18B provide a perspective view (FIG. 18A) and a diagrammatic view (FIG. 18B) of a microfluidic device for monitoring blood biology under flow in an exemplary system for platelet and fibrin related data collection and analysis.
Figure 18B:
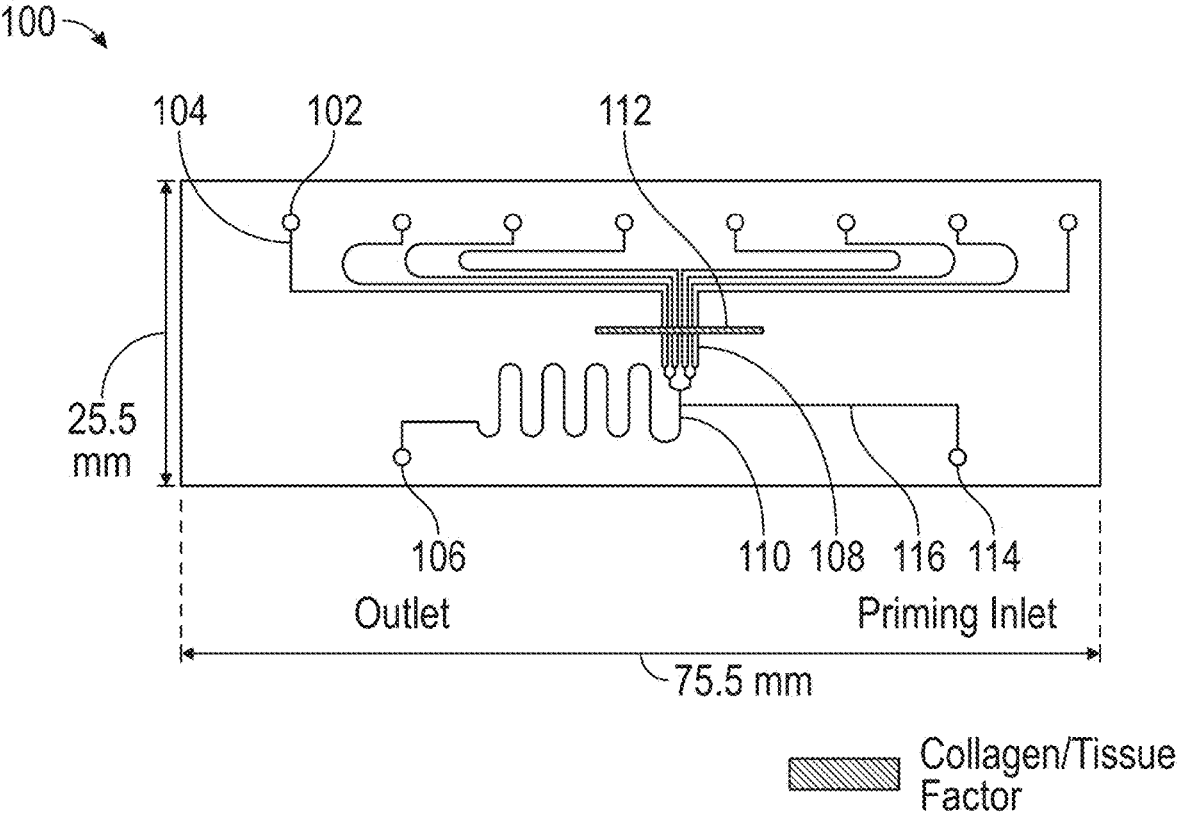

FIG. 18A is a perspective view of a microfluidic device 100 for monitoring blood biology under flow in the exemplary system, and FIG. 18B is a diagrammatic view of the microfluidic device 100. As such, the same reference numbers are used to represent the same structures. The device 100 generally includes microfluidic circuits including multiple inlet ports 102 (e.g., 8 inlet ports), a microfluidic flow path 104 in fluidic communication with each of the inlet ports 102 and leading to a single outlet port 106. In some embodiments, the device 100 can include a single dedicated inlet port for each of the respective inlet ports 102. In some embodiments, the device 100 can include dedicated outlet ports for each of the respective inlet ports 102. The flow paths 104 can all converge, creating an imaging zone 108, before a flow path 110 extends to the outlet 106. In some embodiments, the flow path 110 can be substantially rectilinear. In some embodiments, the flow path 110 can define a serpentine or continuously curving configuration. Critically, all flow paths should be of the same length between inlet and exit to ensure that resistance to flow is consistent between flow paths, and therefore, for a given applied pressure, the flow rates are identical as well.

The device 100 can include a collagen/tissue factor reaction zone 112 positioned at or near the imaging zone 108 of the device 100. Bringing the fluidic paths in proximity to one another simplifies imaging by allowing for imaging of all flow paths/reaction zones within the same field of view (although imaging using multiple fields of view using higher magnification would also be beneficial in some instances). Additional reactants specific to clot formation are also expected to be useful in the reaction zone (e.g. Factor XIa, Kaolin, collagen related peptides, or the like). The imaging zone can also include fiducial marks (both fluorescent and non-fluorescent) that allow for detection and alignment of the reaction zone automatically via the instrument's software.

A priming inlet 114 can be in fluidic communication with a microfluidic priming flow path 116 that connects in a fluidic manner with the outlet flow path 110 at or near the imaging zone 108. In operation, when a priming fluid is applied under pressure to the priming circuit, the priming fluid can flow through the microfluidic flow path 104 to the inlet ports 102 due to low resistance to flow in the microfluidic flow path 104 relative to the outlet 106. Other devices and methods of priming are envisioned, such as those described in International Patent Application Nos. PCT/US2019/022965 and PCT/US2024/014159, which are incorporated herein by reference in their entirety.

In some embodiments, the device 100 can allow for up to eight unique conditions to be tested simultaneously. However, it is envisioned that the device can allow for more than eight, or fewer than eight conditions to be tested simultaneously. Flowing blood over a localized region of collagen and tissue factor 112 can induce clot formation (platelet and fibrin deposition) and allows for sensitivity to any disruption of the hemostasis/coagulation process. The assay test using the device 100 provides the ability to evaluate drug activity in any of the device's flowpaths.

The system can rely on direct fluorescence signals for analysis of the results at the collagen/tissue factor 112. Fresh whole blood (used within minutes of venous draw), AF594 fibrinogen (fibrinogen from human plasma, Alexa Fluor™ 594 conjugate) and platelet MCA2588A488 (mouse anti-human CD61, Alexa Fluor™ 488 conjugate) can be added to the device 100 and the direct fluorescence signals can be analyzed. Chemicals that inhibit specific coagulation pathways, such as corn trypsin inhibitor or PPACK, can also be added to the patient blood (either before or along with the labeling chemicals) to prevent unwanted reactions, such as contact activation of the intrinsic coagulation pathway. The result is the production of direct fluorescent signals in green (platelets) and red (fibrin) where the measured fluorescent intensity (FI) directly correlates with the accumulation of platelets and fibrin. The fluorescent signal intensity can be directly measured at each clot site over time to produce clot response curves for both fibrin and platelets. Fluorescence signal (intensity) can be extracted for each clot and plotted for each assay condition.

The platelet and fibrin label can be added and mixed with the blood prior to addition to the inlet ports 102, or could be added to the inlet ports prior to adding and mixing the blood. It is contemplated that the reagents could also be stored wet or dried/lyophilized within the inlet ports 102 (or other locations within the device) before use. The addition of the blood and mixing of the reagents can be performed manually or automated (pipetting robot) off the device, or could be performed within the device using macro and microfluidic structures known to those in the art.

Figures 19A, 19B, 19C, 19D, 19E:
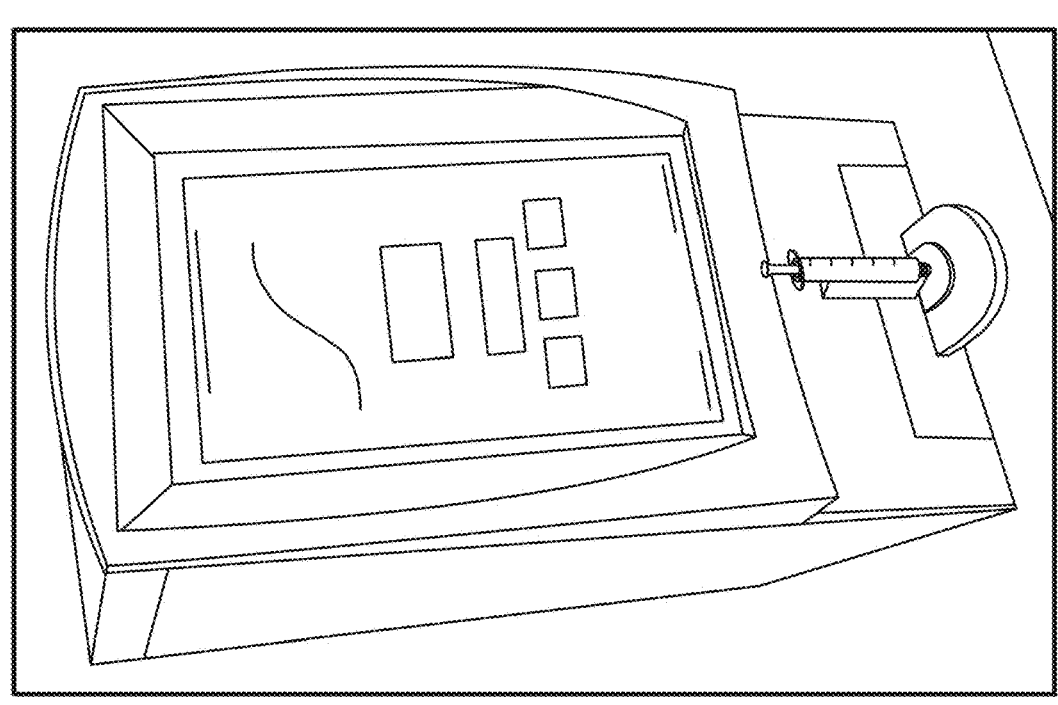
FIGS. 19A-19E are views of an instrument and graphical user interface of a working system for platelet and fibrin data collection and analysis, including a perspective view of the device (FIG. 19A), a user interface for input of a patient ID (FIG. 19B), a user interface for input of an operator ID (FIG. 19C), a user interface for input of a cassette ID (FIG. 19D), and output results of the system (FIG. 19E)

The system (FIG. 19A) can include associated software on a computing or processing device capable of controlling/monitoring use and analysis of the assay device (FIGS. 19B-D) and the data generated by the assay device (FIG. 19E). For example, the system or device can include a user interface capable of receiving input and displaying data generated by the assay device. In some embodiments, the computer is separate from the imaging device, while in other embodiments, the computer is built within the device. The software can control instrument functions, such as camera gain, frame rate, light emitting diode (LED) intensity, pump action, and pressure control, as well as other electro-mechanical functions. Images of clot formation can be shown in real-time via the graphical user interface.

Blood can be drawn from the patient and into a vacutainer or other suitable holding device, such as a syringe. Blood could alternatively be drawn directly into the device through an appropriate connection (e.g. an IV line and Luer connection). The vacutainer can be plugged into the device, and the device can be loaded into an analyzer (e.g., an imaging instrument with computing and software for analyzing the device). Automated analysis can provide results to the medical professional in 15 minutes or less. Useful data from the process of analyzing a sample may be discernible at earlier time points, including as early as 30 seconds into the run. A readout/report can be generated from the data, and provided to the clinician. A user interface on a computer or mobile device can be used to visualize the data in real-time, or a report with information relating to the assay device testing and analysis, e.g., fibrin and platelet function can be created and printed. Additional useful data from the process may be attainable 30 minutes or later after initiation of the analysis (e.g., clot lysis).

Figure 20:
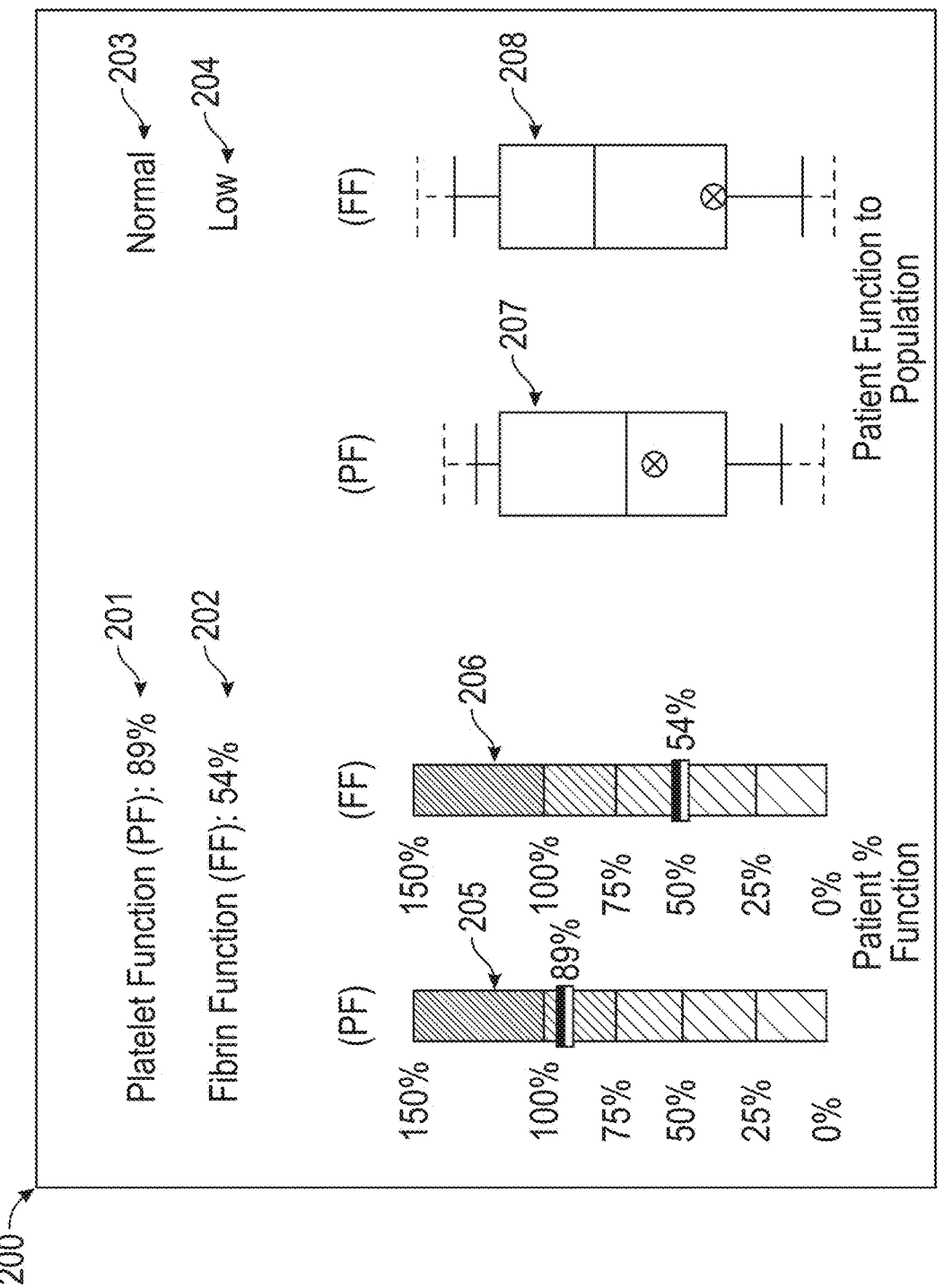
FIG. 20 is a diagrammatic view of a graphical user interface of an exemplary system interface for displaying platelet and fibrin data.

FIG. 20 is a diagrammatic view of a graphical user interface 200 of the exemplary system for displaying results to the clinician based on the automated analysis and determination of the assay device and associated software. The interface 200 can display the platelet percent function in section 201, the fibrin percent function in section 202, the normalcy of the platelet function in section 203, the normalcy of the fibrin function in section 204, a percent platelet function plot in section 205, a percent fibrin function plot in section 206, a platelet function boxplot of the resultant patient data compared to the population data in section 207, and a fibrin function boxplot of the resultant patient data compared to the population data in section 208. The user interface 200 can thereby provide a simple readout of the overall platelet and fibrin function, using both text and graphical display, in comparison to population norms.

Experimentation was performed with the exemplary assay device and system. In particular, testing was performed on, and data was gathered from, samples from volunteer donors and patients.

Two signals are generated in the test as fluorescence intensity (FI) for fibrin and platelets accumulating in the region of interest on the device. In general, at least two and up to eight duplicates for fibrin and platelet signals are taken (although more or less are contemplated in some embodiments). The optimal time at which to select data for analyses is generally determined to be the time of the maximum rate of stable signal development, which typically corresponds to the half-max or T50 time point of the assay. In general the optimum range of FI analysis is typically seen between T25 and T75, or quarter-max and three-quarter-max signal. This selection of time helps avoid signal saturation after T75, and helps avoid delayed initiation prior to T25. The FI value at these times (T25, T50, T75) is referred to as the E25, E50 and E75 FI value respectively, although additional time points may produce useful analysis (5 to 25 minutes). In some embodiments, the time range can be between about, e.g., 1-25 minutes, inclusive, 1-5 minutes inclusive, 5-25 minutes inclusive, 1-60 minutes inclusive, 5-60 minutes inclusive, 25-60 minutes inclusive, or the like. A variety of analyses were performed. The typical performance of the exemplary assay device testing is discussed herein.

The exemplary system provides for the potential for a multiplex, microfluidic, hemodynamic assay, which simulates physiological blood flow and measures the functional components of blood during the clotting process via fluorescent optical detection. The system can be used for in vitro diagnostic use by trained medical professionals at the point-of-care and by laboratory professionals in clinical laboratories.

Results from the exemplary system were collected from 1) 8 healthy normal volunteer donors (total of 20 data points), and 2) from 48 aFib/VTE patients who were prescribed and were taking either rivaroxaban or apixaban DOACs. The data collected from the healthy normal donors served as the healthy normal population data. Donors 5 and 7 had only one device run (two lanes averaged) while all other donors had two devices (two lanes each averaged) run across four separate days. The patient population consisted of 48 patients treated with apixaban or rivaroxaban, analyzed over the course of an approximately 12 month clinical study. The healthy normal donor population were analyzed on devices containing the same level of reactivity in regards to collagen and tissue factor at the reaction zone as the DOAC patient population.

All blood samples were collected into a discard vacutainer. The sample was then immediately treated with corn trypsin inhibitor. Human Alexa 594 fibrinogen and Alexa 488 Anti CD61 antibody were used as the labeling reagents and were added to the CTI treated blood in a tube. The treated blood was then immediately analyzed on the device.

Figure 21A:
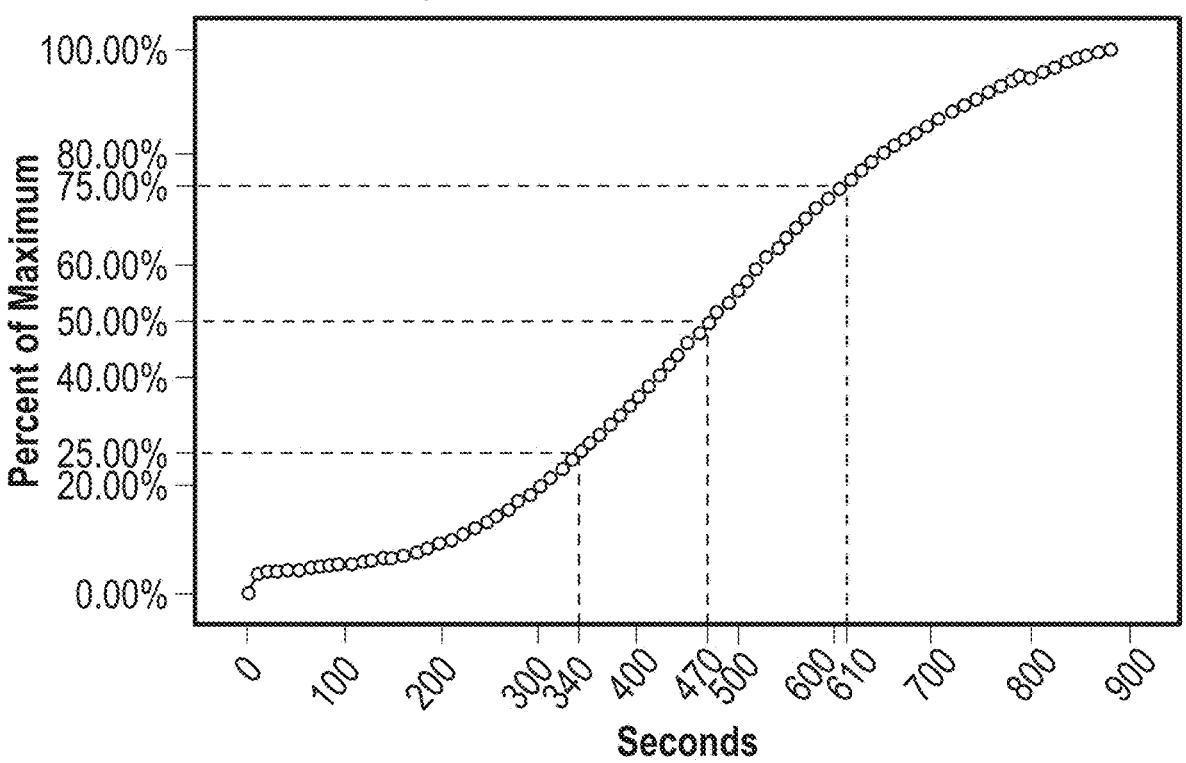
Figure 21B:
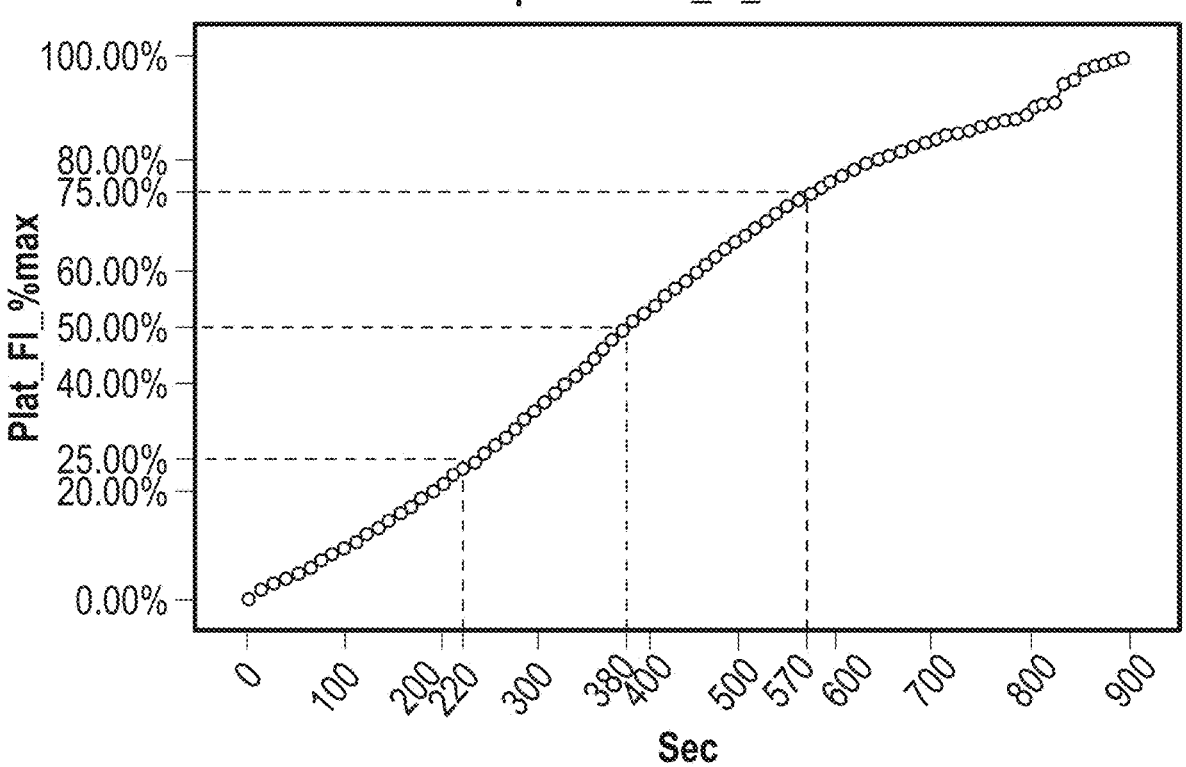

FIGS. 21A-21B show the healthy normal population data with the fibrin and platelet signals averaged, and key time points (T25, T50 T75) denoted for each. Standard statistical analyses were run and standard deviations (SD) around the average were calculated from 0 to 2 SD.

Figures 22A, 22B:
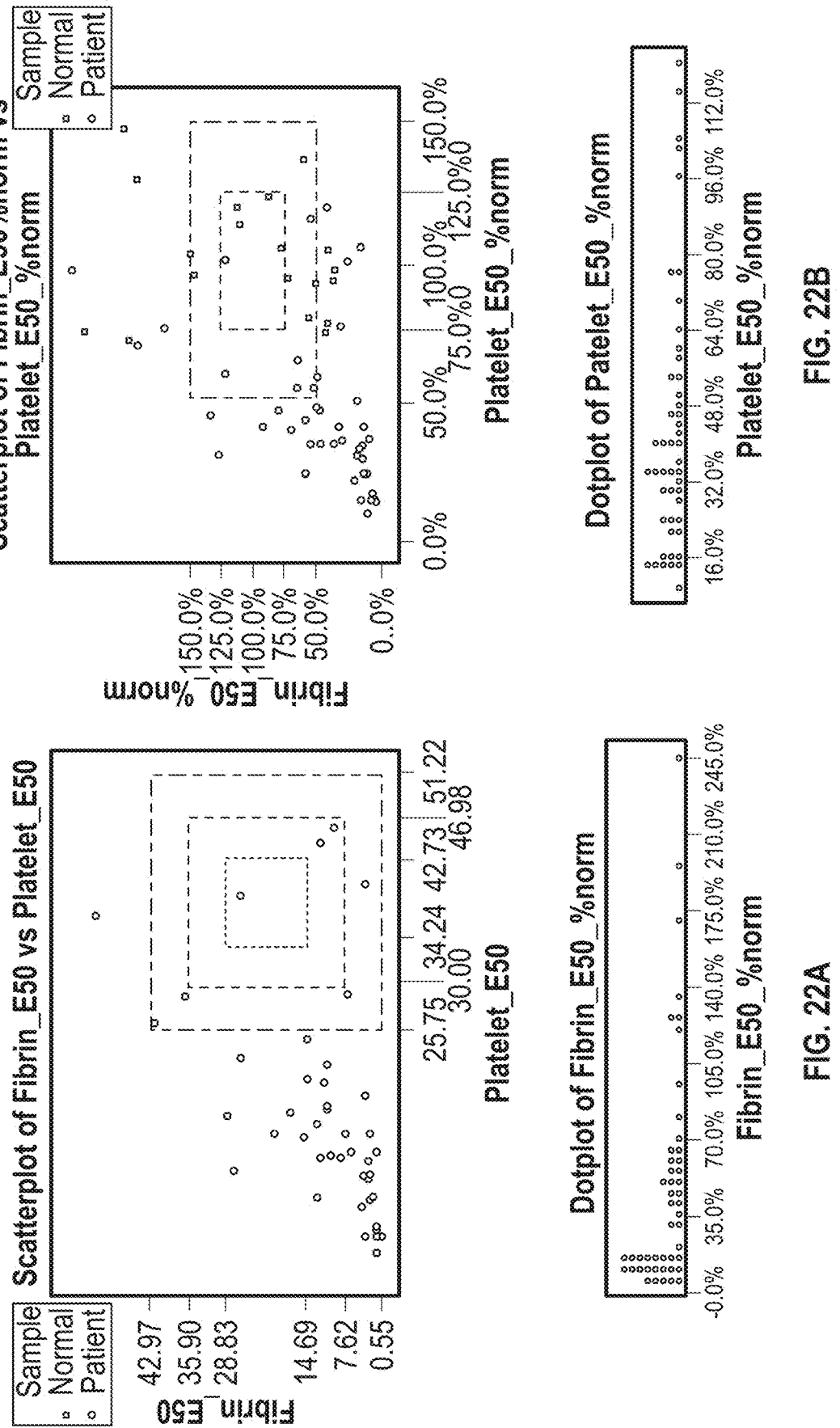
FIGS. 22A-22B are graphs showing the distribution of DOAC treated patient sample platelet and fibrin signals (FIG. 22A), in comparison to "normal" platelet and fibrin signals (FIG. 22B)

FIG. 22A shows a plot of the patient data for both platelet and fibrin RFI, showing the position of each patient sample in relation to the standard deviations of the healthy population data. For example, + or −0.5 SD is indicated by the green box, + or −1.0 SD is designated by the yellow box, and + or −1.5 SD is designated by the red box. This could correspond to a normal (green), high or low normal (yellow) and abnormal (red) assessment of patient platelet and coagulation behavior. FIG. 22B shows the same patient fibrin data presented as a percent of normal ((patient fibrin signal/fibrin population average)*100), in comparison to the healthy normal population data. As can be seen by both FIGS. 22A and 22B, the patients who are on long term DOAC medication show substantively lower fibrin, and platelet signals than the normal population data, as would be expected. Patients that do fall within the normal bounds are likely due to having very low levels of drug present at the time of blood draw.

Figure 23:
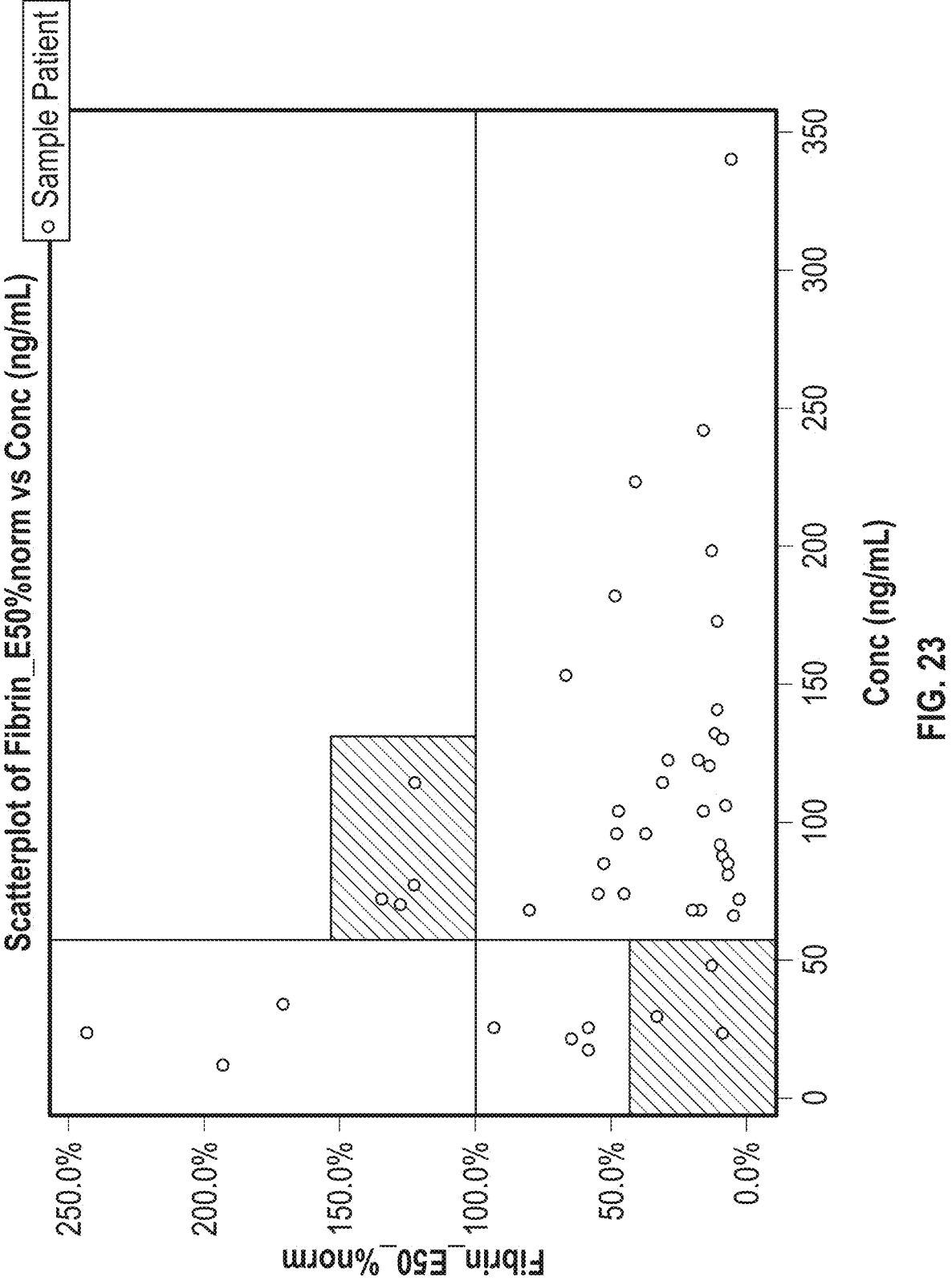
FIG. 23 is a graph showing how the output of the system can be used clinically to distinguish patient samples with abnormal functional fibrin response, in comparison to non-functional assay like, like LCMS derived drug concentration.

In comparison to LCMS calculated drug levels, it is clear that patient samples largely show suppressed fibrin function that is concordant with increasing therapeutic levels of DOAC drugs. However, the exemplary system also shows that some patients' coagulation function has lower activity than expected, based solely on quantitative LCMS derived drug levels, while some patients show higher coagulation activity than would be expected, based solely on quantitative LCMS derived drug levels. (See, e.g., FIG. 23). In particular, combining the percent function estimation for fibrin activity with a quantitative measure of drug levels in a patients' blood, the system can identify functional coagulation problems, even when the measured (LCMS) level of drug would suggest that the patient should have relatively normal clotting function. This demonstrates the utility of the exemplary assay device in determining functional clotting, in comparison to purely quantitative, yet non-physiologic/non-functional assays like LCMS, which cannot evaluate functional state. This difference in determining function over quantity would make a difference in clinical decision making, for example, in terms of whether a patient should receive a reversal drug against the DOAC being taken, or whether the patient should receive blood products to correct a functional defect not caused by the drug being taken. Those patients on therapeutic levels of drug >50 ng/ml) based upon LCMS, that have "normal" coagulation may not require DOAC drug reversal, thereby saving thousands of dollars in unnecessary treatment, and avoiding any complications from administering a drug that was not needed. Likewise, patients demonstrating low doses of drug by LCMS that show highly suppressed coagulation function could very well benefit from drug reversal, or more likely benefit from receiving blood products that can support coagulation function since waiting for the drug to simply wash out may not restore coagulation function for these patients.

The system can be indicated for the assessment of hemostatic function, can aid in the assessment of bleeding and thrombotic risk during restoration of hemostasis with blood products, and can evaluate hemostatic function in patients who are suspected of or treated with drugs that affect platelet or coagulation function. The system can be used with patients in a variety of situations where functional hemostatic evaluation could be useful to have as additional information, e.g., patients experiencing a drug related bleeding episode, patients at risk for major bleeding (such as those undergoing urgent invasive surgery, trauma patients, ischemic stroke patients requiring tPA), or the like. The system could also be used to evaluate drug dosing during initial application of anti-platelet of anti-coagulation drugs, as well as evaluating hemostatic response to long term anti-platelet or anti-coagulation drug use. In some instances, the assay can be used as a companion diagnostic for the development of novel anti-platelet or anti-coagulation drugs and their reversal reversal agents. In some embodiments, the assay can be used can be used as a stand-alone test. In some embodiments, the assay can be used in conjunction with other clinical and laboratory findings.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A system for detecting and quantifying hemostasis function within a biological sample, the system comprising:
   a multi-channel detection instrument programmed to collect, process, analyze and display multiple independent biological signals associated with the biological sample in real time, the multi-channel detection instrument being further programmed with computing capability whereby the multi-channel detection instrument mathematically and statistically compares one or more of the collected multiple independent biological signals associated with the biological sample with a population data set to compute a hemostatic result for the biological sample; and
   an assay device capable of receiving a biological sample, wherein manipulated introduction of the biological sample into the assay device, and physiological flow of the biological sample through the assay device, results in directed biological processes by which clots accumulate at a discrete reaction zone of the assay device;
   wherein the multi-channel detection instrument includes control functionality whereby conditions experienced by the biological sample in the assay device may be varied; and
   wherein the assay device is capable of receiving one or more chemical reagents compatible with the biological sample, and usable for detecting the accumulation of the clots within the reaction zone.

2. The system of claim 1, wherein the biological sample includes platelet specific fluorescent labeling and fibrin specific fluorescent labeling, and comprising a fluorescent assembly capable of detecting the fluorescent labeling of the biological sample, and comprising a processing device configured to receive as input a measurement of a signal associated with the fluorescent labeling of the accumulated clots at the discrete reaction zone of the assay device, and the processing device is configured to correlate a measured fluorescent intensity with the accumulation of the clots in microfluidic flow paths of the assay device, to determine at least one of a platelet function, a coagulation function, a platelet normalcy, a fibrin normalcy, a platelet response to a drug, and/or a coagulation response to a drug, within the biological sample.

3. The system of claim 1, wherein the one or more chemical reagents is a fluorescent reagent capable of labeling fibrin and platelets associated with the clots from the biological sample that results in a fluorescent assembly that reports the accumulation of the clots.

4. The system of claim 3, comprising a light source for monitoring the platelets and fibrin within microfluidic flow paths of the assay device, and for detecting a reaction to the one or more chemical reagents or response to one or more drugs.

5. The system of claim 1, wherein the assay device includes:
   an inlet port configured to receive the biological sample, wherein the biological sample is an unmodified sample including a platelet specific fluorescent label and a fibrin specific fluorescent label;
   an outlet port; and
   microfluidic flow paths fluidically connecting the inlet port with the outlet port;
   wherein the passage of the biological sample through the microfluidic flowpaths generates a platelet signal and a fibrin signal.

6. The system of claim 1, wherein the biological sample comprises a whole blood sample, a processed blood sample, a blood sample treated with an anticoagulant, a blood sample treated with a reagent to prevent intrinsic pathway coagulation activation, a citrated blood sample that is recalcified, a heparinized blood sample treated with protamine, or a blood sample treated with an antiplatelet drug to reduce platelet activation.

7. The system of claim 1, wherein the assay device is capable of receiving one or more drug reagents compatible with the biological sample that may modify the accumulation of the clots within the reaction zone.

8. The system of claim 1, comprising a processing device configured to compare biological sample platelet and fibrin signals to healthy population platelet and fibrin signals, respectively, or diseased population platelet and fibrin signals, respectively, or targeted population platelet and fibrin signals, respectively, to determine a difference in platelet and fibrin activity in comparison to population data.

9. The system of claim 8, wherein a platelet signal and a fibrin signal are compared independently or dependently to each other or the population data, over time or at fixed points in time, or in comparison to one or more thresholds in fluorescent signal, or time.

10. The system of claim 8, comprising a processing device configured to collect the population data for comparison to the biological sample platelet and fibrin signals.

11. The system of claim 8, comprising a processing device configured to use population statistics, mathematical characteristics, and statistical methodologies of the population data to evaluate the biological sample platelet and fibrin signals in comparison to the population data.

12. The system of claim 11, wherein the population statistics, the mathematical characteristics, and the statistical methodologies are used to determine at least one of percent platelet function, percent fibrin function, or categorical determination of normalcy in unmodified and modified samples.

13. The system of claim 8, comprising a processing device configured to monitor a patient over time, in the presence of drugs that affect platelet and fibrin function.

14. The system of claim 1, wherein the clots, and their associated signals, accumulated at the reaction zone of the assay device are usable to determine at least one of a platelet function, a coagulation function, a platelet normalcy, a fibrin normalcy, a platelet response to a drug, or a coagulation response to a drug, within the biological sample.

15. The system of claim 1, wherein at least one of the multiple independent biological signals collected from the biological sample is compared in real-time to the population data set to determine the difference in biological function between the biological sample and the population data set.

16. The system of claim 1, wherein at least one of the multiple independent biological signals collected from the biological sample is analyzed, and wherein at least one of the analyzed biological signals is displayed on the multi-channel detection instrument in real-time so as to convey a diagnostic output.

\* \* \* \* \*